(12) United States Patent
Pope et al.

(10) Patent No.: US 11,696,796 B2
(45) Date of Patent: Jul. 11, 2023

(54) ELECTROSURGICAL SYSTEM

(71) Applicant: Applied Medical Resources Corporation, Rancho Santa Margarita, CA (US)

(72) Inventors: Ryan Pope, Rancho Santa Margarita, CA (US); Kevin Siazon, Rancho Santa Margarita, CA (US); Duy Nguyen, Rancho Santa Margarita, CA (US); Vincent Rodriguez, Rancho Santa Margarita, CA (US); Molly Marbut, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 754 days.

(21) Appl. No.: 16/674,965

(22) Filed: Nov. 5, 2019

(65) Prior Publication Data
US 2020/0155220 A1     May 21, 2020

Related U.S. Application Data

(60) Provisional application No. 62/768,782, filed on Nov. 16, 2018.

(51) Int. Cl.
*A61B 18/12* (2006.01)
*A61B 18/14* (2006.01)
(Continued)

(52) U.S. Cl.
CPC .......... *A61B 18/1206* (2013.01); *A61B 34/25* (2016.02); *A61B 2018/0063* (2013.01);
(Continued)

(58) Field of Classification Search
CPC ........ A61B 18/1206; A61B 2018/0063; A61B 2018/00702; A61B 2018/00714; A61B 2018/00791; A61B 234/25
See application file for complete search history.

(56) References Cited

U.S. PATENT DOCUMENTS

| 371,664 A | 10/1887 | Brannan et al. |
| 702,472 A | 6/1902 | Pignolet |

(Continued)

FOREIGN PATENT DOCUMENTS

| DE | 40 24 636 A1 | 2/1992 |
| DE | 40 24 636 C2 | 12/1992 |

(Continued)

OTHER PUBLICATIONS

European Patent Office, Extended European Search Report for European Application No. EP 21215386.0, dated May 24, 2022, 6 pgs.

(Continued)

*Primary Examiner* — Michael F Peffley
*Assistant Examiner* — Samantha M Good
(74) *Attorney, Agent, or Firm* — Thomas Nguyen; Patrick Ikehara

(57) ABSTRACT

An electrosurgical system is provided and includes a bipolar electrosurgical instrument and an electrosurgical generator. The bipolar electrosurgical instrument is arranged to seal and cut tissue captured between jaws of the bipolar electrosurgical instrument. The electrosurgical generator is arranged to supply RF energy through the bipolar electrosurgical instrument, monitor the supplied RF energy, and adjust or terminate the supplied RF energy to optimally seal the tissue.

34 Claims, 10 Drawing Sheets

(51) Int. Cl.
*A61B 34/00* (2016.01)
*A61B 90/00* (2016.01)
*A61B 18/00* (2006.01)

(52) U.S. Cl.
CPC ............ *A61B 2018/00702* (2013.01); *A61B 2018/00714* (2013.01); *A61B 2018/00791* (2013.01); *A61B 2018/126* (2013.01); *A61B 2018/1266* (2013.01); *A61B 2018/1457* (2013.01); *A61B 2034/258* (2016.02); *A61B 2090/061* (2016.02); *A61B 2090/063* (2016.02)

(56) References Cited

U.S. PATENT DOCUMENTS

| | | |
|---|---|---|
| 728,883 A | 5/1903 | Downes |
| 1,586,645 A | 6/1926 | Bierman |
| 1,935,289 A | 11/1933 | Evans |
| 2,002,594 A | 5/1935 | Wappler et al. |
| 2,031,682 A | 2/1936 | Wappler et al. |
| 2,113,246 A | 4/1938 | Wappler |
| 2,176,479 A | 10/1939 | Willis |
| 2,305,156 A | 12/1942 | Grubel |
| 2,632,661 A | 3/1953 | Cristofv |
| 2,827,056 A | 3/1958 | Degelman |
| 3,085,566 A | 4/1963 | Tolles |
| 3,459,187 A | 8/1969 | Pallotta |
| 3,494,363 A | 2/1970 | Jackson |
| 3,588,710 A | 6/1971 | Masters |
| 3,651,811 A | 3/1972 | Hildebrandt et al. |
| 3,685,518 A | 8/1972 | Beuerle et al. |
| 3,780,416 A | 12/1973 | Rider |
| 3,826,263 A | 7/1974 | Cage et al. |
| 3,911,766 A | 10/1975 | Fridolph et al. |
| 3,920,021 A | 11/1975 | Hiltebrandt |
| 3,938,527 A | 2/1976 | Rioux et al. |
| 3,963,030 A | 6/1976 | Newton |
| 3,970,088 A | 7/1976 | Morrison |
| 3,980,085 A | 9/1976 | Ikuno |
| 3,987,795 A | 10/1976 | Morrison |
| 4,030,501 A | 6/1977 | Archibald |
| 4,041,952 A | 8/1977 | Morrison, Jr. et al. |
| 4,043,342 A | 8/1977 | Morrison, Jr. |
| 4,060,088 A | 11/1977 | Morrison, Jr. et al. |
| 4,074,718 A | 2/1978 | Morrison, Jr. |
| 4,089,336 A | 5/1978 | Cage et al. |
| 4,092,986 A | 6/1978 | Schneiderman |
| 4,094,320 A | 6/1978 | Newton et al. |
| 4,114,623 A | 9/1978 | Meinke et al. |
| 4,126,137 A | 11/1978 | Archibald |
| 4,154,240 A | 5/1979 | Ikuno et al. |
| 4,171,700 A | 10/1979 | Farin |
| 4,181,131 A | 1/1980 | Ogui |
| 4,188,927 A | 2/1980 | Harris |
| 4,196,734 A | 4/1980 | Harris |
| 4,198,957 A | 4/1980 | Cage et al. |
| 4,198,960 A | 4/1980 | Utsugi |
| 4,200,104 A | 4/1980 | Harris |
| 4,231,372 A | 11/1980 | Newton |
| 4,237,887 A | 12/1980 | Gonser |
| 4,244,371 A | 1/1981 | Farin |
| 4,325,374 A | 4/1982 | Komiya |
| 4,331,149 A | 5/1982 | Gonser |
| 4,338,940 A | 7/1982 | Ikuno |
| 4,352,156 A | 9/1982 | Gyugyi |
| 4,370,980 A | 2/1983 | Lottick |
| 4,416,276 A | 11/1983 | Newton et al. |
| 4,416,277 A | 11/1983 | Newton et al. |
| 4,427,014 A | 1/1984 | Bel et al. |
| 4,429,694 A | 2/1984 | McGreevy |
| 4,463,759 A | 8/1984 | Garito et al. |
| 4,487,489 A | 12/1984 | Takamatsu |
| 4,514,619 A | 4/1985 | Kugelman |
| 4,522,206 A | 6/1985 | Whipple et al. |
| 4,552,143 A | 11/1985 | Lottick |
| 4,569,131 A | 2/1986 | Faulk et al. |
| 4,569,345 A | 2/1986 | Manes |
| 4,590,934 A | 5/1986 | Malis et al. |
| 4,599,553 A | 7/1986 | Brennen et al. |
| 4,630,218 A | 12/1986 | Hurley |
| 4,632,109 A | 12/1986 | Paterson |
| 4,644,950 A | 2/1987 | Valli |
| 4,651,280 A | 3/1987 | Chang et al. |
| 4,655,216 A | 4/1987 | Tischer |
| 4,657,018 A | 4/1987 | Hakky |
| 4,658,815 A | 4/1987 | Farin et al. |
| 4,658,819 A | 4/1987 | Harris et al. |
| 4,658,820 A | 4/1987 | Klicek |
| 4,674,498 A | 6/1987 | Stasz |
| 4,685,459 A | 8/1987 | Koch et al. |
| 4,699,146 A | 10/1987 | Sieverding |
| 4,712,545 A | 12/1987 | Honkanen |
| 4,716,897 A | 1/1988 | Noguchi et al. |
| 4,727,874 A | 3/1988 | Bowers et al. |
| 4,739,759 A | 4/1988 | Rexroth et al. |
| 4,741,334 A | 5/1988 | Irnich |
| 4,752,864 A | 6/1988 | Clappier |
| 4,754,757 A | 7/1988 | Feucht |
| 4,788,977 A | 12/1988 | Farin et al. |
| 4,802,476 A | 2/1989 | Noerenberg et al. |
| 4,818,954 A | 4/1989 | Flachenecker et al. |
| 4,827,927 A | 5/1989 | Newton |
| 4,848,335 A | 7/1989 | Manes |
| 4,850,353 A | 7/1989 | Stasz et al. |
| 4,860,745 A | 8/1989 | Farin et al. |
| 4,862,889 A | 9/1989 | Feucht |
| 4,862,890 A | 9/1989 | Stasz et al. |
| 4,872,456 A | 10/1989 | Hasson |
| 4,887,612 A | 12/1989 | Esser et al. |
| 4,889,722 A | 12/1989 | Sheffield et al. |
| 4,903,696 A | 2/1990 | Stasz et al. |
| 4,905,691 A | 3/1990 | Rydell |
| 4,922,903 A | 5/1990 | Welch et al. |
| 4,936,281 A | 6/1990 | Stasz |
| 4,937,254 A | 6/1990 | Sheffield et al. |
| 4,938,761 A | 7/1990 | Ensslin |
| 4,942,313 A | 7/1990 | Kinzel |
| 4,958,539 A | 9/1990 | Stasz et al. |
| 4,969,885 A | 11/1990 | Farin |
| 4,976,711 A | 12/1990 | Parins et al. |
| 5,007,908 A | 4/1991 | Rydell |
| 5,013,312 A | 5/1991 | Parins et al. |
| 5,015,227 A | 5/1991 | Broadwin et al. |
| 5,016,521 A | 5/1991 | Haka |
| 5,026,370 A | 6/1991 | Lottick |
| 5,026,371 A | 6/1991 | Rydell et al. |
| 5,035,696 A | 7/1991 | Rydell |
| 5,038,109 A | 8/1991 | Goble et al. |
| 5,047,026 A | 9/1991 | Rydell |
| 5,047,027 A | 9/1991 | Rydell |
| 5,052,402 A | 10/1991 | Bencini et al. |
| 5,057,107 A | 10/1991 | Parins et al. |
| 5,061,269 A | 10/1991 | Muller |
| 5,062,031 A | 10/1991 | Flachenecker et al. |
| 5,071,419 A | 12/1991 | Rydell et al. |
| 5,078,717 A | 1/1992 | Parins et al. |
| 5,083,565 A | 1/1992 | Parins |
| 5,085,659 A | 2/1992 | Rydell |
| 5,087,257 A | 2/1992 | Farin et al. |
| 5,098,431 A | 3/1992 | Rydell |
| 5,116,332 A | 5/1992 | Lottick |
| 5,122,137 A | 6/1992 | Lennox |
| 5,125,928 A | 6/1992 | Parins et al. |
| 5,127,412 A | 7/1992 | Cosmetto et al. |
| 5,151,102 A | 9/1992 | Kamiyama et al. |
| 5,158,561 A | 10/1992 | Rydell et al. |
| 5,160,343 A | 11/1992 | Brancel et al. |
| 5,167,658 A | 12/1992 | Ensslin |
| 5,171,255 A | 12/1992 | Rydell |
| 5,171,311 A | 12/1992 | Rydell |
| 5,190,517 A | 3/1993 | Zieve et al. |
| 5,190,541 A | 3/1993 | Abele et al. |
| 5,192,280 A | 3/1993 | Parins |
| 5,197,963 A | 3/1993 | Parins |
| 5,197,964 A | 3/1993 | Parins |

(56) References Cited

U.S. PATENT DOCUMENTS

| | | |
|---|---|---|
| 5,201,732 A | 4/1993 | Parins et al. |
| 5,217,457 A | 6/1993 | Delahuerga et al. |
| 5,217,458 A | 6/1993 | Parins |
| 5,234,427 A | 8/1993 | Ohtomo et al. |
| 5,244,462 A | 9/1993 | Delahuerga et al. |
| 5,246,440 A | 9/1993 | Van Noord |
| 5,250,047 A | 10/1993 | Rydell |
| 5,250,056 A | 10/1993 | Hasson |
| 5,254,126 A | 10/1993 | Filipi et al. |
| 5,256,149 A | 10/1993 | Banik et al. |
| 5,258,006 A | 11/1993 | Rydell et al. |
| 5,267,997 A | 12/1993 | Farin et al. |
| 5,269,780 A | 12/1993 | Roos |
| 5,273,524 A | 12/1993 | Fox et al. |
| 5,281,216 A | 1/1994 | Klicek |
| 5,282,799 A | 2/1994 | Rydell |
| 5,286,255 A | 2/1994 | Weber |
| 5,290,286 A | 3/1994 | Parins |
| 5,300,070 A | 4/1994 | Gentelia et al. |
| 5,304,190 A | 4/1994 | Reckelhoff et al. |
| 5,312,329 A | 5/1994 | Beaty et al. |
| 5,314,424 A | 5/1994 | Nicholas |
| 5,318,563 A | 6/1994 | Malis et al. |
| 5,322,055 A | 6/1994 | Davison et al. |
| 5,324,289 A | 6/1994 | Eggers |
| 5,330,471 A | 7/1994 | Eggers |
| 5,334,183 A | 8/1994 | Wuchinich |
| 5,338,317 A | 8/1994 | Hasson et al. |
| 5,341,807 A | 8/1994 | Nardella |
| 5,341,815 A | 8/1994 | Cofone et al. |
| 5,342,359 A | 8/1994 | Rydell |
| 5,342,381 A | 8/1994 | Tidemand |
| 5,352,222 A | 10/1994 | Rydell |
| 5,352,223 A | 10/1994 | McBrayer et al. |
| 5,354,313 A | 10/1994 | Boebel |
| 5,356,408 A | 10/1994 | Rydell |
| 5,370,645 A | 12/1994 | Klicek et al. |
| 5,372,124 A | 12/1994 | Takayama et al. |
| 5,372,596 A | 12/1994 | Klicek et al. |
| 5,374,277 A | 12/1994 | Hassler |
| 5,382,247 A | 1/1995 | Cimino et al. |
| 5,383,880 A | 1/1995 | Hooven |
| 5,383,922 A | 1/1995 | Zipes et al. |
| 5,387,196 A | 2/1995 | Green et al. |
| 5,387,197 A | 2/1995 | Smith et al. |
| 5,389,104 A | 2/1995 | Hahnen et al. |
| 5,389,849 A | 2/1995 | Asano et al. |
| 5,391,166 A | 2/1995 | Eggers |
| 5,392,917 A | 2/1995 | Alpern et al. |
| 5,400,267 A | 3/1995 | Denen et al. |
| 5,403,312 A | 4/1995 | Yates et al. |
| 5,403,342 A | 4/1995 | Tovey et al. |
| 5,405,344 A | 4/1995 | Willaimson et al. |
| 5,409,498 A | 4/1995 | Braddock et al. |
| 5,417,687 A | 5/1995 | Nardella et al. |
| 5,422,567 A | 6/1995 | Matsunaga |
| 5,423,808 A | 6/1995 | Edwards et al. |
| 5,423,810 A | 6/1995 | Goble et al. |
| 5,431,638 A | 7/1995 | Hennig et al. |
| 5,431,649 A | 7/1995 | Mulier et al. |
| 5,431,674 A | 7/1995 | Basile et al. |
| 5,432,459 A | 7/1995 | Thompson et al. |
| 5,436,566 A | 7/1995 | Thompson et al. |
| 5,437,664 A | 8/1995 | Cohen et al. |
| 5,438,302 A | 8/1995 | Goble |
| 5,443,463 A | 8/1995 | Stern et al. |
| 5,445,142 A | 8/1995 | Hassler, Jr. |
| 5,445,638 A | 8/1995 | Rydell et al. |
| 5,447,513 A | 9/1995 | Davison et al. |
| 5,449,355 A | 9/1995 | Rhum et al. |
| 5,456,684 A | 10/1995 | Schmidt et al. |
| 5,458,598 A | 10/1995 | Feinberg et al. |
| 5,460,182 A | 10/1995 | Goodman et al. |
| 5,462,546 A | 10/1995 | Rydell |
| 5,464,144 A | 11/1995 | Guy et al. |
| 5,472,439 A | 12/1995 | Hurd |
| 5,472,442 A | 12/1995 | Klicek |
| 5,472,443 A | 12/1995 | Cordis et al. |
| 5,472,451 A | 12/1995 | Freitas et al. |
| 5,474,057 A | 12/1995 | Makower et al. |
| 5,476,479 A | 12/1995 | Green et al. |
| 5,478,351 A | 12/1995 | Meade et al. |
| 5,484,400 A | 1/1996 | Edwards et al. |
| 5,486,185 A | 1/1996 | Freitas et al. |
| 5,496,312 A | 3/1996 | Klicek |
| 5,496,317 A | 3/1996 | Goble et al. |
| 5,499,992 A | 3/1996 | Meade et al. |
| 5,499,998 A | 3/1996 | Meade et al. |
| 5,503,320 A | 4/1996 | Webster et al. |
| 5,507,773 A | 4/1996 | Huitema et al. |
| 5,509,916 A | 4/1996 | Taylor |
| 5,514,129 A | 5/1996 | Smith |
| 5,514,134 A | 5/1996 | Rydell et al. |
| 5,518,163 A | 5/1996 | Hooven |
| 5,518,164 A | 5/1996 | Hooven |
| 5,527,313 A | 6/1996 | Scott et al. |
| 5,527,330 A | 6/1996 | Tovey |
| 5,531,744 A | 7/1996 | Nardella et al. |
| 5,540,681 A | 7/1996 | Strul et al. |
| 5,540,684 A | 7/1996 | Hassler, Jr. |
| 5,540,685 A | 7/1996 | Parins et al. |
| 5,541,376 A | 7/1996 | Ladtkow et al. |
| 5,551,945 A | 9/1996 | Yabe et al. |
| 5,558,429 A | 9/1996 | Cain |
| 5,558,671 A | 9/1996 | Yates |
| 5,562,699 A | 10/1996 | Heimberger et al. |
| 5,562,700 A | 10/1996 | Huitema et al. |
| 5,571,100 A | 11/1996 | Goble et al. |
| 5,571,121 A | 11/1996 | Heifetz |
| 5,573,424 A | 11/1996 | Poppe |
| 5,573,533 A | 11/1996 | Strul |
| 5,573,534 A | 11/1996 | Stone |
| 5,573,535 A | 11/1996 | Viklund |
| 5,575,789 A | 11/1996 | Bell et al. |
| 5,575,805 A | 11/1996 | Li |
| 5,584,830 A | 12/1996 | Ladd et al. |
| 5,599,344 A | 2/1997 | Paterson |
| 5,599,350 A | 2/1997 | Schulze et al. |
| 5,603,711 A | 2/1997 | Parins et al. |
| D378,611 S | 3/1997 | Croley |
| 5,607,391 A | 3/1997 | Klinger et al. |
| 5,609,151 A | 3/1997 | Mulier et al. |
| 5,609,560 A | 3/1997 | Ichikawa et al. |
| 5,609,573 A | 3/1997 | Sandock |
| 5,611,709 A | 3/1997 | McAnulty |
| 5,613,966 A | 3/1997 | Makower et al. |
| 5,620,415 A | 4/1997 | Lucey et al. |
| 5,620,447 A | 4/1997 | Smith et al. |
| 5,624,452 A | 4/1997 | Yates |
| 5,626,575 A | 5/1997 | Crermer |
| 5,626,607 A | 5/1997 | Malecki et al. |
| 5,626,608 A | 5/1997 | Cuny et al. |
| 5,627,584 A | 5/1997 | Nishikori et al. |
| 5,633,578 A | 5/1997 | Eggers et al. |
| 5,645,540 A | 7/1997 | Henniges et al. |
| 5,647,869 A | 7/1997 | Goble et al. |
| 5,651,780 A | 7/1997 | Jackson et al. |
| 5,658,279 A | 8/1997 | Nardella et al. |
| 5,658,281 A | 8/1997 | Heard |
| 5,665,100 A | 9/1997 | Yoon |
| 5,665,105 A | 9/1997 | Furnish et al. |
| 5,667,517 A | 9/1997 | Hooven |
| 5,669,907 A | 9/1997 | Platt, Jr. et al. |
| 5,674,184 A | 10/1997 | Hassler, Jr. |
| 5,674,220 A | 10/1997 | Fox et al. |
| 5,683,349 A | 11/1997 | Makower et al. |
| 5,688,270 A | 11/1997 | Yates et al. |
| 5,693,045 A | 12/1997 | Eggers |
| 5,693,051 A | 12/1997 | Schulze et al. |
| 5,695,494 A | 12/1997 | Becker |
| 5,697,281 A | 12/1997 | Eggers et al. |
| 5,697,909 A | 12/1997 | Eggers et al. |
| 5,700,261 A | 12/1997 | Brinkerhoff |
| 5,702,386 A | 12/1997 | Stern et al. |

(56) References Cited

U.S. PATENT DOCUMENTS

| | | |
|---|---|---|
| 5,702,387 A | 12/1997 | Arts et al. |
| 5,702,390 A | 12/1997 | Austin et al. |
| 5,707,369 A | 1/1998 | Vaitekunas et al. |
| 5,709,680 A | 1/1998 | Yates et al. |
| 5,713,128 A | 2/1998 | Schrenk et al. |
| 5,713,895 A | 2/1998 | Lontine et al. |
| 5,713,896 A | 2/1998 | Nardella |
| 5,720,742 A | 2/1998 | Quinn et al. |
| 5,720,744 A | 2/1998 | Eggleston et al. |
| 5,720,745 A | 2/1998 | Farin et al. |
| 5,722,975 A | 3/1998 | Edwards et al. |
| 5,725,524 A | 3/1998 | Mulier et al. |
| 5,735,848 A | 4/1998 | Yates et al. |
| 5,735,849 A | 4/1998 | Baden et al. |
| 5,743,456 A | 4/1998 | Jones et al. |
| 5,743,906 A | 4/1998 | Parins et al. |
| 5,746,210 A | 5/1998 | Benaron et al. |
| 5,746,740 A | 5/1998 | Nicholas |
| 5,746,759 A | 5/1998 | Meade et al. |
| 5,752,519 A | 5/1998 | Benaron et al. |
| 5,755,717 A | 5/1998 | Yates et al. |
| 5,759,185 A | 6/1998 | Grinberg |
| 5,762,609 A | 6/1998 | Benaron et al. |
| 5,766,167 A | 6/1998 | Eggers et al. |
| 5,769,791 A | 6/1998 | Benaron et al. |
| 5,769,841 A | 6/1998 | Odell et al. |
| 5,772,597 A | 6/1998 | Goldberger et al. |
| 5,772,659 A | 6/1998 | Becker et al. |
| 5,772,660 A | 6/1998 | Young et al. |
| 5,776,092 A | 7/1998 | Farin et al. |
| 5,776,129 A | 7/1998 | Mersch |
| 5,776,130 A | 7/1998 | Buysse et al. |
| 5,776,155 A | 7/1998 | Beaupre et al. |
| 5,782,397 A | 7/1998 | Koukline |
| 5,785,658 A | 7/1998 | Benaron et al. |
| 5,792,139 A | 8/1998 | Chambers et al. |
| 5,792,178 A | 8/1998 | Welch et al. |
| 5,797,906 A | 8/1998 | Rhum et al. |
| 5,797,938 A | 8/1998 | Paraschac et al. |
| 5,797,941 A | 8/1998 | Schulze et al. |
| 5,800,449 A | 9/1998 | Wales |
| 5,807,261 A | 9/1998 | Benaron et al. |
| 5,807,393 A | 9/1998 | Williamson, IV et al. |
| 5,807,395 A | 9/1998 | Mulier et al. |
| 5,810,806 A | 9/1998 | Ritchart et al. |
| 5,810,811 A | 9/1998 | Yates et al. |
| 5,810,859 A | 9/1998 | DiMatteo et al. |
| 5,817,091 A | 10/1998 | Nardella et al. |
| 5,817,093 A | 10/1998 | Williamson, IV et al. |
| 5,817,119 A | 10/1998 | Klieman et al. |
| 5,827,271 A | 10/1998 | Buysse et al. |
| 5,827,279 A | 10/1998 | Hughett et al. |
| 5,827,299 A | 10/1998 | Thomason et al. |
| 5,830,231 A | 11/1998 | Geiges, Jr. |
| 5,833,690 A | 11/1998 | Yates et al. |
| 5,836,942 A | 11/1998 | Netherly et al. |
| 5,836,943 A | 11/1998 | Miller, III |
| 5,846,194 A | 12/1998 | Wasson et al. |
| 5,849,020 A | 12/1998 | Long et al. |
| 5,853,412 A | 12/1998 | Mayenberger |
| 5,860,975 A | 1/1999 | Goble et al. |
| 5,873,873 A | 2/1999 | Smith et al. |
| 5,876,398 A | 3/1999 | Mulier et al. |
| 5,876,401 A | 3/1999 | Schulze et al. |
| 5,885,277 A | 3/1999 | Korth |
| 5,891,095 A | 4/1999 | Eggers et al. |
| 5,891,141 A | 4/1999 | Rydell |
| 5,891,142 A | 4/1999 | Eggers et al. |
| 5,893,835 A | 4/1999 | Witt et al. |
| 5,893,873 A | 4/1999 | Rader et al. |
| 5,897,490 A | 4/1999 | Fox et al. |
| 5,897,523 A | 4/1999 | Wright et al. |
| 5,897,553 A | 4/1999 | Mulier et al. |
| 5,897,569 A | 4/1999 | Kellogg et al. |
| 5,902,264 A | 5/1999 | Toso et al. |
| 5,902,301 A | 5/1999 | Olig |
| 5,904,709 A | 5/1999 | Arndt et al. |
| 5,906,613 A | 5/1999 | Mulier et al. |
| 5,908,402 A | 6/1999 | Blythe |
| 5,908,420 A | 6/1999 | Parins et al. |
| 5,910,152 A | 6/1999 | Bays |
| 5,928,137 A | 7/1999 | Green |
| 5,928,255 A | 7/1999 | Meade et al. |
| 5,928,256 A | 7/1999 | Riza |
| 5,931,836 A | 8/1999 | Hatta et al. |
| 5,935,126 A | 8/1999 | Riza |
| 5,938,633 A | 8/1999 | Beaupre |
| 5,944,715 A | 8/1999 | Goble et al. |
| 5,944,718 A | 8/1999 | Austin et al. |
| 5,944,737 A | 8/1999 | Tsonton et al. |
| 5,947,284 A | 9/1999 | Foster |
| 5,947,984 A | 9/1999 | Whipple |
| 5,951,552 A | 9/1999 | Long et al. |
| 5,954,736 A | 9/1999 | Bishop et al. |
| 5,954,746 A | 9/1999 | Holthaus et al. |
| 5,957,943 A | 9/1999 | Vaitekunas |
| 5,961,514 A | 10/1999 | Long et al. |
| 5,968,062 A | 10/1999 | Thomas et al. |
| 5,968,074 A | 10/1999 | Prestel |
| 5,976,077 A | 11/1999 | Wittens et al. |
| 5,976,128 A | 11/1999 | Schilling et al. |
| 5,980,510 A | 11/1999 | Tsonton et al. |
| 5,980,516 A | 11/1999 | Mulier et al. |
| 5,984,921 A | 11/1999 | Long et al. |
| 5,987,346 A | 11/1999 | Benaron et al. |
| 5,993,380 A | 11/1999 | Yabe et al. |
| 5,993,447 A | 11/1999 | Blewett et al. |
| 5,995,875 A | 11/1999 | Blewett et al. |
| 5,997,533 A | 12/1999 | Kuhns |
| 6,003,517 A | 12/1999 | Sheffield et al. |
| 6,004,319 A | 12/1999 | Goble et al. |
| 6,004,335 A | 12/1999 | Vaitekunas et al. |
| 6,010,499 A | 1/2000 | Cobb |
| 6,010,516 A | 1/2000 | Hulka |
| 6,013,076 A | 1/2000 | Goble et al. |
| 6,015,406 A | 1/2000 | Goble et al. |
| 6,016,809 A | 1/2000 | Mulier et al. |
| D420,741 S | 2/2000 | Croley |
| 6,024,741 A | 2/2000 | Williamson, IV et al. |
| 6,024,744 A | 2/2000 | Kese et al. |
| 6,027,501 A | 2/2000 | Goble et al. |
| 6,027,522 A | 2/2000 | Palmer |
| 6,030,384 A | 2/2000 | Nezhat |
| 6,030,402 A | 2/2000 | Thompson et al. |
| 6,033,399 A | 3/2000 | Gines |
| 6,033,404 A | 3/2000 | Melzer et al. |
| 6,036,657 A | 3/2000 | Milliman et al. |
| 6,039,733 A | 3/2000 | Buysse et al. |
| 6,039,734 A | 3/2000 | Goble |
| 6,039,736 A | 3/2000 | Platt, Jr. |
| 6,050,996 A | 4/2000 | Schmaltz et al. |
| 6,051,010 A | 4/2000 | DiMatteo et al. |
| 6,053,172 A | 4/2000 | Hovda et al. |
| 6,053,914 A | 4/2000 | Eggers et al. |
| 6,056,746 A | 5/2000 | Goble et al. |
| 6,063,050 A | 5/2000 | Manna et al. |
| 6,063,075 A | 5/2000 | Mihori |
| 6,063,081 A | 5/2000 | Mulier et al. |
| 6,063,086 A | 5/2000 | Benecke et al. |
| 6,066,139 A | 5/2000 | Ryan et al. |
| 6,068,627 A | 5/2000 | Orszulak et al. |
| 6,068,647 A | 5/2000 | Witt et al. |
| 6,070,444 A | 6/2000 | Lontine et al. |
| 6,074,386 A | 6/2000 | Goble et al. |
| RE36,795 E | 7/2000 | Rydell |
| 6,083,191 A | 7/2000 | Rose |
| 6,086,586 A | 7/2000 | Hooven |
| 6,090,106 A | 7/2000 | Goble et al. |
| 6,090,120 A | 7/2000 | Wright et al. |
| 6,092,722 A | 7/2000 | Heinrichs et al. |
| 6,093,186 A | 7/2000 | Goble |
| 6,096,037 A | 8/2000 | Mulier et al. |
| 6,102,909 A | 8/2000 | Chen et al. |
| 6,106,521 A | 8/2000 | Blewett et al. |

(56) References Cited

U.S. PATENT DOCUMENTS

| | | |
|---|---|---|
| 6,109,268 A | 8/2000 | Thapliyal et al. |
| 6,110,171 A | 8/2000 | Rydell |
| 6,113,591 A | 9/2000 | Whayne et al. |
| 6,113,594 A | 9/2000 | Savage |
| 6,113,596 A | 9/2000 | Hooven et al. |
| 6,113,598 A | 9/2000 | Baker |
| 6,117,152 A | 9/2000 | Huitema |
| 6,120,501 A | 9/2000 | Long et al. |
| H1904 H | 10/2000 | Yates |
| 6,132,429 A | 10/2000 | Baker |
| 6,135,998 A | 10/2000 | Palanker |
| 6,139,519 A | 10/2000 | Blythe |
| 6,139,547 A | 10/2000 | Lontine et al. |
| 6,142,992 A | 11/2000 | Cheng et al. |
| 6,152,923 A | 11/2000 | Ryan |
| 6,159,146 A | 12/2000 | El Gazayerli |
| 6,162,235 A | 12/2000 | Vaitekunas |
| 6,165,175 A | 12/2000 | Wampler et al. |
| 6,168,605 B1 | 1/2001 | Measamer et al. |
| 6,171,304 B1 | 1/2001 | Netherly et al. |
| 6,174,308 B1 | 1/2001 | Goble et al. |
| 6,174,309 B1 | 1/2001 | Wrublewski et al. |
| 6,179,834 B1 | 1/2001 | Buysse et al. |
| 6,186,147 B1 | 2/2001 | Cobb |
| 6,187,003 B1 | 2/2001 | Buysse et al. |
| 6,187,026 B1 | 2/2001 | Devlin et al. |
| 6,190,383 B1 | 2/2001 | Schmaltz et al. |
| 6,190,385 B1 | 2/2001 | Tom et al. |
| 6,190,386 B1 | 2/2001 | Rydell |
| 6,193,129 B1 | 2/2001 | Bittner et al. |
| 6,193,653 B1 | 2/2001 | Evans et al. |
| 6,193,713 B1 | 2/2001 | Geistert et al. |
| 6,197,026 B1 | 3/2001 | Farin et al. |
| 6,203,541 B1 | 3/2001 | Keppel |
| 6,206,823 B1 | 3/2001 | Kolata et al. |
| 6,206,844 B1 | 3/2001 | Reichel et al. |
| 6,206,875 B1 | 3/2001 | Long et al. |
| 6,206,877 B1 | 3/2001 | Kese et al. |
| 6,210,403 B1 | 4/2001 | Klicek |
| 6,210,405 B1 | 4/2001 | Goble et al. |
| 6,214,003 B1 | 4/2001 | Morgan et al. |
| 6,214,023 B1 | 4/2001 | Whipple et al. |
| 6,228,023 B1 | 5/2001 | Zaslavsky et al. |
| 6,228,055 B1 | 5/2001 | Foerster et al. |
| 6,228,080 B1 | 5/2001 | Gines |
| 6,228,081 B1 | 5/2001 | Goble |
| 6,228,083 B1 | 5/2001 | Lands et al. |
| 6,234,178 B1 | 5/2001 | Goble et al. |
| 6,237,604 B1 | 5/2001 | Burnside et al. |
| 6,238,366 B1 | 5/2001 | Savage et al. |
| 6,238,392 B1 | 5/2001 | Long |
| 6,238,393 B1 | 5/2001 | Mulier et al. |
| 6,242,741 B1 | 6/2001 | Miller et al. |
| 6,246,912 B1 | 6/2001 | Sluijter et al. |
| 6,251,106 B1 | 6/2001 | Becker et al. |
| 6,251,110 B1 | 6/2001 | Wampler |
| 6,254,623 B1 | 7/2001 | Haibel, Jr. et al. |
| 6,257,241 B1 | 7/2001 | Wampler |
| 6,258,085 B1 | 7/2001 | Eggleston |
| 6,261,286 B1 | 7/2001 | Goble et al. |
| 6,267,761 B1 | 7/2001 | Ryan |
| 6,270,497 B1 | 8/2001 | Sekino et al. |
| 6,273,862 B1 | 8/2001 | Privitera et al. |
| 6,277,114 B1 | 8/2001 | Bullivant et al. |
| 6,277,115 B1 | 8/2001 | Saadat |
| 6,277,117 B1 | 8/2001 | Tetzlaff et al. |
| 6,280,398 B1 | 8/2001 | Ritchart et al. |
| 6,280,407 B1 | 8/2001 | Manna et al. |
| 6,280,441 B1 | 8/2001 | Ryan |
| 6,283,963 B1 | 9/2001 | Regula |
| 6,287,344 B1 | 9/2001 | Wampler |
| 6,293,942 B1 | 9/2001 | Goble et al. |
| 6,293,945 B1 | 9/2001 | Parins et al. |
| 6,296,637 B1 | 10/2001 | Thorne et al. |
| 6,296,640 B1 | 10/2001 | Wampler et al. |
| 6,298,550 B1 | 10/2001 | Kirwan, Jr. |
| 6,302,903 B1 | 10/2001 | Mulier et al. |
| 6,306,131 B1 | 10/2001 | Hareyama et al. |
| 6,306,134 B1 | 10/2001 | Goble et al. |
| 6,308,089 B1 | 10/2001 | von der Ruhr et al. |
| 6,309,400 B2 | 10/2001 | Beaupre |
| 6,312,426 B1 | 11/2001 | Goldberg et al. |
| 6,315,777 B1 | 11/2001 | Comben |
| 6,319,221 B1 | 11/2001 | Savage et al. |
| 6,322,494 B1 | 11/2001 | Bullivant et al. |
| 6,322,549 B1 | 11/2001 | Eggers et al. |
| 6,322,561 B1 | 11/2001 | Eggers et al. |
| 6,325,795 B1 | 12/2001 | Lindemann et al. |
| 6,325,799 B1 | 12/2001 | Goble |
| 6,325,811 B1 | 12/2001 | Messerly |
| 6,328,736 B1 | 12/2001 | Mulier et al. |
| 6,328,751 B1 | 12/2001 | Beaupre |
| 6,331,181 B1 | 12/2001 | Tierney et al. |
| 6,334,068 B1 | 12/2001 | Hacker |
| 6,334,861 B1 | 1/2002 | Chandler et al. |
| 6,336,926 B1 | 1/2002 | Goble |
| 6,348,051 B1 | 2/2002 | Farin et al. |
| 6,352,532 B1 | 3/2002 | Kramer et al. |
| 6,352,536 B1 | 3/2002 | Buysse et al. |
| 6,358,248 B1 | 3/2002 | Mulier et al. |
| 6,358,249 B1 | 3/2002 | Chen et al. |
| 6,358,267 B1 | 3/2002 | Murakami |
| 6,361,534 B1 | 3/2002 | Chen et al. |
| 6,364,877 B1 | 4/2002 | Goble et al. |
| 6,364,879 B1 | 4/2002 | Chen et al. |
| 6,371,967 B1 | 4/2002 | Long et al. |
| D457,958 S | 5/2002 | Dycus et al. |
| 6,383,183 B1 | 5/2002 | Sekino et al. |
| 6,387,092 B1 | 5/2002 | Burnside et al. |
| 6,387,109 B1 | 5/2002 | Davison et al. |
| 6,391,024 B1 | 5/2002 | Sun et al. |
| 6,391,025 B1 | 5/2002 | Weinstein et al. |
| 6,398,779 B1 | 6/2002 | Buysse et al. |
| 6,398,781 B1 | 6/2002 | Goble et al. |
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,747 B1 | 6/2002 | Lindemann et al. |
| 6,402,748 B1 | 6/2002 | Schoenman et al. |
| 6,406,475 B1 | 6/2002 | Wenzler et al. |
| 6,409,722 B1 | 6/2002 | Hoey et al. |
| 6,409,724 B1 | 6/2002 | Penny et al. |
| 6,409,728 B1 | 6/2002 | Ehr et al. |
| 6,416,486 B1 | 7/2002 | Wampler |
| 6,416,509 B1 | 7/2002 | Goble et al. |
| 6,423,057 B1 | 7/2002 | He et al. |
| 6,423,082 B1 | 7/2002 | Houser et al. |
| 6,432,118 B1 | 8/2002 | Messerly |
| 6,436,096 B1 | 8/2002 | Hareyama |
| 6,440,130 B1 | 8/2002 | Mulier et al. |
| 6,443,952 B1 | 9/2002 | Mulier et al. |
| 6,443,968 B1 | 9/2002 | Holthaus et al. |
| 6,443,970 B1 | 9/2002 | Schulze et al. |
| 6,451,013 B1 | 9/2002 | Bays et al. |
| 6,451,018 B1 | 9/2002 | Lands et al. |
| 6,454,764 B1 | 9/2002 | Fleenor et al. |
| 6,454,781 B1 | 9/2002 | Witt et al. |
| 6,454,782 B1 | 9/2002 | Schwemberger |
| 6,458,078 B1 | 10/2002 | Lüdtke et al. |
| 6,458,128 B1 | 10/2002 | Schulze |
| 6,458,130 B1 | 10/2002 | Frazier et al. |
| 6,458,142 B1 | 10/2002 | Faller et al. |
| 6,461,352 B2 | 10/2002 | Morgan et al. |
| 6,464,689 B1 | 10/2002 | Qin et al. |
| 6,464,702 B2 | 10/2002 | Schulze et al. |
| 6,464,704 B2 | 10/2002 | Schmaltz et al. |
| 6,468,275 B1 | 10/2002 | Wampler et al. |
| 6,468,286 B2 | 10/2002 | Mastri et al. |
| 6,475,217 B1 | 11/2002 | Platt |
| 6,478,030 B1 | 11/2002 | Shapeton et al. |
| 6,482,202 B1 | 11/2002 | Goble et al. |
| 6,485,490 B2 | 11/2002 | Wampler et al. |
| 6,488,507 B1 | 12/2002 | Stoloff et al. |
| 6,488,680 B1 | 12/2002 | Francischelli et al. |

(56) References Cited

U.S. PATENT DOCUMENTS

| | | |
|---|---|---|
| 6,491,690 B1 | 12/2002 | Goble et al. |
| 6,491,708 B2 | 12/2002 | Madan et al. |
| 6,493,589 B1 | 12/2002 | Medhkour et al. |
| 6,494,877 B2 | 12/2002 | Odell et al. |
| 6,494,902 B2 | 12/2002 | Hoey et al. |
| 6,497,705 B2 | 12/2002 | Comben |
| 6,500,176 B1 | 12/2002 | Truckai et al. |
| 6,500,188 B2 | 12/2002 | Harper et al. |
| 6,503,263 B2 | 1/2003 | Adams |
| 6,506,189 B1 | 1/2003 | Rittman, III et al. |
| 6,506,208 B2 | 1/2003 | Hunt et al. |
| 6,510,854 B2 | 1/2003 | Goble et al. |
| 6,511,476 B2 | 1/2003 | Hareyama |
| 6,511,480 B1 | 1/2003 | Tetzlaff et al. |
| 6,514,252 B2 | 2/2003 | Nezhat et al. |
| 6,517,536 B2 | 2/2003 | Hooven et al. |
| 6,517,538 B1 | 2/2003 | Jacob et al. |
| 6,526,320 B2 | 2/2003 | Mitchell |
| 6,527,771 B1 | 3/2003 | Weadock et al. |
| 6,533,784 B2 | 3/2003 | Truckai et al. |
| 6,534,770 B2 | 3/2003 | Miller et al. |
| 6,537,248 B2 | 3/2003 | Mulier et al. |
| 6,537,272 B2 | 3/2003 | Christopherson et al. |
| 6,540,695 B1 | 4/2003 | Burbank et al. |
| 6,543,456 B1 | 4/2003 | Freeman |
| 6,547,783 B1 | 4/2003 | Vilendrer et al. |
| 6,547,786 B1 | 4/2003 | Goble et al. |
| 6,554,829 B2 | 4/2003 | Schulze et al. |
| 6,558,379 B1 | 5/2003 | Batchelor et al. |
| 6,558,383 B2 | 5/2003 | Cunningham et al. |
| 6,561,983 B2 | 5/2003 | Cronin et al. |
| 6,562,037 B2 | 5/2003 | Paton et al. |
| 6,565,559 B2 | 5/2003 | Eggleston |
| 6,565,560 B1 | 5/2003 | Goble et al. |
| 6,569,105 B1 | 5/2003 | Kortenbach et al. |
| 6,569,109 B2 | 5/2003 | Sakurai et al. |
| 6,572,615 B2 | 6/2003 | Schulze et al. |
| 6,579,289 B2 | 6/2003 | Schnitzler |
| 6,582,424 B2 | 6/2003 | Fleenor et al. |
| 6,582,427 B1 | 6/2003 | Goble et al. |
| 6,584,360 B2 | 6/2003 | Francischelli et al. |
| D477,408 S | 7/2003 | Bromley |
| 6,585,732 B2 | 7/2003 | Mulier et al. |
| 6,585,733 B2 | 7/2003 | Wellman |
| 6,585,735 B1 | 7/2003 | Frazier et al. |
| 6,589,200 B1 | 7/2003 | Schwemberger et al. |
| 6,591,719 B1 | 7/2003 | Poole et al. |
| 6,592,582 B2 | 7/2003 | Hess et al. |
| 6,594,518 B1 | 7/2003 | Benaron et al. |
| 6,602,227 B1 | 8/2003 | Cimino et al. |
| 6,602,249 B1 | 8/2003 | Stoddard et al. |
| 6,602,252 B2 | 8/2003 | Mollenauer |
| 6,605,036 B1 | 8/2003 | Wild |
| 6,607,529 B1 | 8/2003 | Jones et al. |
| 6,610,060 B2 | 8/2003 | Mulier et al. |
| 6,611,793 B1 | 8/2003 | Burnside et al. |
| 6,613,048 B2 | 9/2003 | Mulier et al. |
| 6,616,656 B2 | 9/2003 | Brommersma |
| 6,616,660 B1 | 9/2003 | Platt |
| 6,616,661 B2 | 9/2003 | Wellman et al. |
| 6,620,157 B1 | 9/2003 | Dabney et al. |
| 6,620,161 B2 | 9/2003 | Schulze et al. |
| 6,623,482 B2 | 9/2003 | Pendekanti et al. |
| 6,623,515 B2 | 9/2003 | Mulier et al. |
| 6,626,901 B1 | 9/2003 | Treat et al. |
| 6,629,974 B2 | 10/2003 | Penny et al. |
| 6,638,274 B2 | 10/2003 | Yamamoto |
| 6,648,883 B2 | 11/2003 | Francischelli et al. |
| 6,652,514 B2 | 11/2003 | Ellman et al. |
| 6,652,521 B2 | 11/2003 | Schulze |
| 6,656,110 B1 | 12/2003 | Irion et al. |
| 6,656,175 B2 | 12/2003 | Francischelli et al. |
| 6,656,176 B2 | 12/2003 | Hess et al. |
| 6,656,177 B2 | 12/2003 | Truckai et al. |
| 6,660,017 B2 | 12/2003 | Beaupre |
| 6,662,050 B2 | 12/2003 | Olson |
| 6,662,127 B2 | 12/2003 | Wiener et al. |
| 6,663,622 B1 | 12/2003 | Foley et al. |
| 6,663,627 B2 | 12/2003 | Francischelli et al. |
| 6,663,628 B2 | 12/2003 | Peters |
| 6,666,865 B2 | 12/2003 | Platt |
| 6,676,660 B2 | 1/2004 | Wampler et al. |
| 6,678,621 B2 | 1/2004 | Wiener et al. |
| 6,679,882 B1 | 1/2004 | Kornerup |
| 6,682,527 B2 | 1/2004 | Strul |
| 6,682,528 B2 | 1/2004 | Frazier et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,692,450 B1 | 2/2004 | Coleman |
| 6,692,489 B1 | 2/2004 | Heim et al. |
| 6,695,837 B2 | 2/2004 | Howell |
| 6,695,838 B2 | 2/2004 | Wellman et al. |
| 6,695,840 B2 | 2/2004 | Schulze |
| 6,699,240 B2 | 3/2004 | Francischelli |
| 6,706,038 B2 | 3/2004 | Francischelli et al. |
| 6,706,039 B2 | 3/2004 | Mulier et al. |
| 6,709,432 B2 | 3/2004 | Ferek-Petric |
| 6,723,091 B2 | 4/2004 | Goble et al. |
| 6,726,683 B1 | 4/2004 | Shaw |
| 6,726,686 B2 | 4/2004 | Buysse et al. |
| 6,733,498 B2 | 5/2004 | Paton et al. |
| 6,736,810 B2 | 5/2004 | Hoey et al. |
| 6,740,084 B2 | 5/2004 | Ryan |
| 6,740,085 B2 | 5/2004 | Hareyama et al. |
| 6,740,102 B2 | 5/2004 | Hess et al. |
| 6,743,229 B2 | 6/2004 | Buysse et al. |
| 6,752,804 B2 | 6/2004 | Simpson et al. |
| 6,755,825 B2 | 6/2004 | Schoenman et al. |
| 6,755,827 B2 | 6/2004 | Mulier et al. |
| 6,755,841 B2 | 6/2004 | Fraser et al. |
| 6,758,846 B2 | 7/2004 | Goble et al. |
| 6,764,487 B2 | 7/2004 | Mulier et al. |
| 6,770,071 B2 | 8/2004 | Woloszko et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,444 B2 | 8/2004 | Messerly |
| 6,775,575 B2 | 8/2004 | Bommannan et al. |
| 6,776,780 B2 | 8/2004 | Mulier et al. |
| 6,780,180 B1 | 8/2004 | Goble et al. |
| 6,786,906 B1 | 9/2004 | Cobb |
| 6,790,217 B2 | 9/2004 | Schulze et al. |
| 6,796,828 B2 | 9/2004 | Ehr et al. |
| 6,796,981 B2 | 9/2004 | Wham et al. |
| 6,807,444 B2 | 10/2004 | Tu et al. |
| 6,807,968 B2 | 10/2004 | Francischelli et al. |
| 6,808,518 B2 | 10/2004 | Wellman et al. |
| 6,808,525 B2 | 10/2004 | Latterell et al. |
| 6,814,745 B2 | 11/2004 | Prestel |
| 6,821,273 B2 | 11/2004 | Mollenauer |
| 6,827,715 B2 | 12/2004 | Francischelli et al. |
| 6,827,717 B2 | 12/2004 | Brommersma et al. |
| 6,827,725 B2 | 12/2004 | Batchelor et al. |
| 6,830,569 B2 | 12/2004 | Thompson et al. |
| 6,832,111 B2 | 12/2004 | Tu et al. |
| 6,832,985 B2 | 12/2004 | Irion et al. |
| 6,832,998 B2 | 12/2004 | Goble |
| 6,835,082 B2 | 12/2004 | Gonnering |
| 6,835,195 B2 | 12/2004 | Schulze et al. |
| 6,837,887 B2 | 1/2005 | Woloszko et al. |
| 6,843,789 B2 | 1/2005 | Goble |
| 6,849,073 B2 | 2/2005 | Hoey et al. |
| 6,852,112 B2 | 2/2005 | Platt |
| 6,855,142 B2 | 2/2005 | Harano et al. |
| 6,855,145 B2 | 2/2005 | Ciarrocca |
| 6,858,028 B2 | 2/2005 | Mulier et al. |
| 6,860,881 B2 | 3/2005 | Sturm et al. |
| 6,860,894 B1 | 3/2005 | Pittman |
| 6,887,240 B1 | 5/2005 | Lands et al. |
| 6,889,694 B2 | 5/2005 | Hooven |
| 6,893,435 B2 | 5/2005 | Goble |
| 6,893,441 B2 | 5/2005 | Brommersma et al. |

(56) References Cited

U.S. PATENT DOCUMENTS

| | | |
|---|---|---|
| 6,899,710 B2 | 5/2005 | Hooven |
| 6,905,497 B2 | 6/2005 | Truckai et al. |
| 6,905,498 B2 | 6/2005 | Hooven |
| 6,908,472 B2 | 6/2005 | Wiener et al. |
| 6,911,019 B2 | 6/2005 | Mulier et al. |
| 6,913,579 B2 | 7/2005 | Truckai et al. |
| 6,916,318 B2 | 7/2005 | Francischelli et al. |
| 6,918,880 B2 | 7/2005 | Brookner et al. |
| 6,923,803 B2 | 8/2005 | Goble |
| 6,923,804 B2 | 8/2005 | Eggers et al. |
| 6,923,806 B2 | 8/2005 | Hooven et al. |
| 6,926,716 B2 | 8/2005 | Baker et al. |
| 6,929,641 B2 | 8/2005 | Goble et al. |
| 6,929,644 B2 | 8/2005 | Truckai et al. |
| 6,932,810 B2 | 8/2005 | Ryan |
| 6,932,811 B2 | 8/2005 | Hooven et al. |
| 6,937,033 B2 | 8/2005 | Boronkay et al. |
| 6,939,347 B2 | 9/2005 | Thompson |
| 6,942,660 B2 | 9/2005 | Pantera et al. |
| 6,942,662 B2 | 9/2005 | Goble et al. |
| 6,945,972 B2 | 9/2005 | Frigg et al. |
| 6,945,981 B2 | 9/2005 | Donofrio et al. |
| 6,948,503 B2 | 9/2005 | Refior et al. |
| 6,949,098 B2 | 9/2005 | Mulier et al. |
| 6,958,063 B1 | 10/2005 | Soil et al. |
| 6,960,209 B2 | 11/2005 | Clague et al. |
| 6,960,210 B2 | 11/2005 | Lands et al. |
| 6,962,587 B2 | 11/2005 | Johnson et al. |
| 6,962,589 B2 | 11/2005 | Mulier et al. |
| 6,966,907 B2 | 11/2005 | Goble |
| 6,966,909 B2 | 11/2005 | Marshall et al. |
| 6,971,988 B2 | 12/2005 | Orban, III |
| 6,974,453 B2 | 12/2005 | Woloszko et al. |
| 6,974,454 B2 | 12/2005 | Hooven |
| 6,976,969 B2 | 12/2005 | Messerly |
| 6,979,332 B2 | 12/2005 | Adams |
| 6,984,231 B2 | 1/2006 | Goble et al. |
| 6,984,233 B2 | 1/2006 | Hooven |
| 6,984,826 B2 | 1/2006 | Miller et al. |
| 6,989,010 B2 | 1/2006 | Francischelli et al. |
| 6,994,705 B2 | 2/2006 | Nobis et al. |
| 6,997,735 B2 | 2/2006 | Ehr et al. |
| 6,997,935 B2 | 2/2006 | Anderson et al. |
| 7,001,380 B2 | 2/2006 | Goble |
| 7,001,415 B2 | 2/2006 | Hooven |
| 7,011,657 B2 | 3/2006 | Truckai et al. |
| 7,025,764 B2 | 4/2006 | Paton et al. |
| 7,029,470 B2 | 4/2006 | Francischelli et al. |
| 7,033,351 B2 | 4/2006 | Howell |
| 7,033,354 B2 | 4/2006 | Keppel |
| 7,033,356 B2 | 4/2006 | Latterell et al. |
| 7,041,096 B2 | 5/2006 | Malis et al. |
| 7,041,102 B2 | 5/2006 | Truckai et al. |
| 7,044,948 B2 | 5/2006 | Keppel |
| 7,044,949 B2 | 5/2006 | Orszulak et al. |
| 7,044,950 B2 | 5/2006 | Yamamoto |
| 7,048,687 B1 | 5/2006 | Reuss et al. |
| 7,049,599 B2 | 5/2006 | Miller et al. |
| 7,052,494 B2 | 5/2006 | Goble et al. |
| 7,060,063 B2 | 6/2006 | Marion et al. |
| 7,063,699 B2 | 6/2006 | Hess et al. |
| 7,066,933 B2 | 6/2006 | Hagg |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,054 B2 | 8/2006 | Truckai et al. |
| 7,090,673 B2 | 8/2006 | Dycus et al. |
| 7,094,202 B2 | 8/2006 | Nobis et al. |
| 7,094,235 B2 | 8/2006 | Francischelli |
| 7,097,644 B2 | 8/2006 | Long |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,104,834 B2 | 9/2006 | Robinson et al. |
| 7,104,989 B2 | 9/2006 | Skarda |
| 7,108,695 B2 | 9/2006 | Witt et al. |
| 7,111,769 B2 | 9/2006 | Wales et al. |
| 7,112,201 B2 | 9/2006 | Truckai et al. |
| RE39,358 E | 10/2006 | Goble |
| 7,116,157 B2 | 10/2006 | Ross et al. |
| 7,118,564 B2 | 10/2006 | Ritchie et al. |
| 7,118,570 B2 | 10/2006 | Tetzlaff et al. |
| 7,118,587 B2 | 10/2006 | Dycus et al. |
| 7,119,516 B2 | 10/2006 | Denning |
| 7,124,932 B2 | 10/2006 | Isaacson |
| 7,125,409 B2 | 10/2006 | Truckai et al. |
| 7,126,125 B2 | 10/2006 | Miller et al. |
| 7,131,445 B2 | 11/2006 | Amoah |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,020 B2 | 11/2006 | Lawes et al. |
| 7,137,980 B2 | 11/2006 | Buysse et al. |
| D533,942 S | 12/2006 | Kerr et al. |
| 7,147,635 B2 | 12/2006 | Ciarrocca |
| 7,147,637 B2 | 12/2006 | Goble |
| 7,147,638 B2 | 12/2006 | Chapman et al. |
| 7,150,097 B2 | 12/2006 | Sremcich et al. |
| 7,150,748 B2 | 12/2006 | Ebbutt et al. |
| 7,150,749 B2 | 12/2006 | Dycus et al. |
| 7,153,300 B2 | 12/2006 | Goble |
| 7,156,843 B2 | 1/2007 | Skarda |
| 7,156,845 B2 | 1/2007 | Mulier et al. |
| 7,156,846 B2 | 1/2007 | Dycus et al. |
| 7,159,750 B2 | 1/2007 | Racenet et al. |
| 7,160,293 B2 | 1/2007 | Sturm et al. |
| 7,160,298 B2 | 1/2007 | Lawes et al. |
| 7,160,299 B2 | 1/2007 | Baily |
| 7,163,548 B2 | 1/2007 | Stulen et al. |
| 7,166,105 B2 | 1/2007 | Mulier et al. |
| 7,169,115 B2 | 1/2007 | Nobis et al. |
| 7,169,144 B2 | 1/2007 | Hoey et al. |
| 7,169,145 B2 | 1/2007 | Isaacson et al. |
| 7,169,146 B2 | 1/2007 | Truckai et al. |
| 7,172,591 B2 | 2/2007 | Harano et al. |
| 7,179,254 B2 | 2/2007 | Pendkanti et al. |
| 7,179,258 B2 | 2/2007 | Buysse et al. |
| 7,182,604 B2 | 2/2007 | Ehr et al. |
| 7,186,252 B2 | 3/2007 | Nobis et al. |
| 7,186,253 B2 | 3/2007 | Truckai et al. |
| 7,187,790 B2 | 3/2007 | Sabol et al. |
| 7,189,231 B2 | 3/2007 | Clague et al. |
| 7,189,232 B2 | 3/2007 | Scholl et al. |
| 7,189,233 B2 | 3/2007 | Truckai et al. |
| 7,191,015 B2 | 3/2007 | Lamson et al. |
| 7,195,627 B2 | 3/2007 | Amoah et al. |
| 7,195,630 B2 | 3/2007 | Ciarrocca |
| 7,195,631 B2 | 3/2007 | Dumbauld |
| 7,204,835 B2 | 4/2007 | Latterell et al. |
| 7,207,471 B2 | 4/2007 | Heinrich et al. |
| 7,207,990 B2 | 4/2007 | Lands et al. |
| D541,938 S | 5/2007 | Kerr et al. |
| 7,211,081 B2 | 5/2007 | Goble |
| 7,211,084 B2 | 5/2007 | Goble et al. |
| 7,214,224 B2 | 5/2007 | Goble |
| 7,216,001 B2 | 5/2007 | Hacker et al. |
| 7,220,260 B2 | 5/2007 | Fleming et al. |
| 7,220,951 B2 | 5/2007 | Truckai et al. |
| 7,223,239 B2 | 5/2007 | Schulze et al. |
| 7,223,265 B2 | 5/2007 | Keppel |
| 7,226,447 B2 | 6/2007 | Uchida et al. |
| 7,229,307 B2 | 6/2007 | Ehr et al. |
| 7,232,439 B2 | 6/2007 | Ciarrocca |
| 7,232,440 B2 | 6/2007 | Dumbauld et al. |
| 7,235,048 B2 | 6/2007 | Rein et al. |
| 7,235,072 B2 | 6/2007 | Sartor et al. |
| 7,235,073 B1 | 6/2007 | Levine et al. |
| 7,237,708 B1 | 7/2007 | Guy et al. |

(56) References Cited

U.S. PATENT DOCUMENTS

| | | |
|---|---|---|
| 7,241,296 B2 | 7/2007 | Buysse et al. |
| 7,247,141 B2 | 7/2007 | Makin et al. |
| 7,247,155 B2 | 7/2007 | Hoey et al. |
| 7,250,048 B2 | 7/2007 | Francischelli et al. |
| 7,250,051 B2 | 7/2007 | Francischelli |
| 7,252,667 B2 | 8/2007 | Moses et al. |
| 7,255,694 B2 | 8/2007 | Keppel |
| 7,255,696 B2 | 8/2007 | Goble et al. |
| 7,255,697 B2 | 8/2007 | Dycus et al. |
| 7,259,340 B2 | 8/2007 | Blaha et al. |
| 7,261,711 B2 | 8/2007 | Mulier et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,273,483 B2 | 9/2007 | Weiner et al. |
| 7,276,068 B2 | 10/2007 | Johnson et al. |
| 7,278,994 B2 | 10/2007 | Goble |
| 7,282,048 B2 | 10/2007 | Goble et al. |
| 7,282,049 B2 | 10/2007 | Oraszulak et al. |
| 7,291,161 B2 | 11/2007 | Hooven |
| 7,297,145 B2 | 11/2007 | Woloszko et al. |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,557 B2 | 12/2007 | Wham et al. |
| 7,309,325 B2 | 12/2007 | Mulier et al. |
| 7,309,849 B2 | 12/2007 | Truckai et al. |
| 7,311,560 B2 | 12/2007 | Ehr et al. |
| 7,311,706 B2 | 12/2007 | Schoenman et al. |
| 7,311,707 B2 | 12/2007 | Hagg et al. |
| 7,311,709 B2 | 12/2007 | Truckai et al. |
| 7,322,975 B2 | 1/2008 | Goble et al. |
| 7,329,256 B2 | 2/2008 | Johnson et al. |
| 7,335,997 B2 | 2/2008 | Weiner |
| 7,344,532 B2 | 3/2008 | Goble et al. |
| 7,347,858 B2 | 3/2008 | Francischelli et al. |
| RE40,279 E | 4/2008 | Sluijter et al. |
| D567,943 S | 4/2008 | Moses et al. |
| 7,353,068 B2 | 4/2008 | Tanaka et al. |
| 7,354,435 B2 | 4/2008 | Farin et al. |
| 7,354,440 B2 | 4/2008 | Truckai et al. |
| 7,354,443 B2 | 4/2008 | Moll et al. |
| 7,364,577 B2 | 4/2008 | Wham et al. |
| 7,364,578 B2 | 4/2008 | Francischelli et al. |
| 7,364,579 B2 | 4/2008 | Mulier et al. |
| 7,367,972 B2 | 5/2008 | Francischelli et al. |
| 7,367,976 B2 | 5/2008 | Lawes et al. |
| 7,371,246 B2 | 5/2008 | Viola |
| 7,377,902 B2 | 5/2008 | Burbank et al. |
| 7,377,918 B2 | 5/2008 | Amoah |
| 7,377,920 B2 | 5/2008 | Buysse et al. |
| RE40,388 E | 6/2008 | Gines |
| 7,381,209 B2 | 6/2008 | Truckai et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,416,101 B2 | 8/2008 | Shelton, IV et al. |
| 7,416,437 B2 | 8/2008 | Sartor et al. |
| 7,419,487 B2 | 9/2008 | Johnson et al. |
| 7,422,139 B2 | 9/2008 | Shelton, IV et al. |
| 7,422,588 B2 | 9/2008 | Mulier et al. |
| 7,424,965 B2 | 9/2008 | Racenet et al. |
| 7,425,835 B2 | 9/2008 | Eisele |
| 7,426,415 B2 | 9/2008 | Kühner |
| 7,431,720 B2 | 10/2008 | Pendekanti et al. |
| 7,431,721 B2 | 10/2008 | Paton et al. |
| 7,435,249 B2 | 10/2008 | Buysse et al. |
| 7,435,250 B2 | 10/2008 | Francischelli et al. |
| 7,442,167 B2 | 10/2008 | Dunki-Jacobs et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,458,972 B2 | 12/2008 | Keppel |
| 7,464,846 B2 | 12/2008 | Shelton, IV et al. |
| 7,470,272 B2 | 12/2008 | Mulier et al. |
| 7,473,250 B2 | 1/2009 | Makin et al. |
| 7,473,253 B2 | 1/2009 | Dycus et al. |
| 7,476,233 B1 | 1/2009 | Wiener et al. |
| 7,481,808 B2 | 1/2009 | Koyfman et al. |
| 7,491,199 B2 | 2/2009 | Goble |
| 7,497,858 B2 | 3/2009 | Chapelon et al. |
| 7,811,283 B2 | 10/2010 | Moses et al. |
| 7,841,765 B2 | 11/2010 | Keller |
| 8,561,615 B2 | 10/2013 | Pannell et al. |
| 8,784,417 B2 | 7/2014 | Hanna |
| 8,808,288 B2 | 8/2014 | Rescheke |
| 9,161,813 B2 | 10/2015 | Benamou |
| 2001/0037110 A1 | 11/2001 | Schmaltz et al. |
| 2001/0039417 A1 | 11/2001 | Harano et al. |
| 2002/0052599 A1 | 5/2002 | Goble |
| 2002/0115997 A1 | 8/2002 | Truckai et al. |
| 2002/0120262 A1 | 8/2002 | Bek et al. |
| 2002/0120266 A1 | 8/2002 | Truckai et al. |
| 2002/0128650 A1 | 9/2002 | McClurken |
| 2002/0151884 A1 | 10/2002 | Hoey et al. |
| 2002/0161363 A1 | 10/2002 | Fodor et al. |
| 2002/0165541 A1 | 11/2002 | Whitman |
| 2002/0188294 A1 | 12/2002 | Couture et al. |
| 2003/0004510 A1 | 1/2003 | Wham et al. |
| 2003/0014052 A1 | 1/2003 | Buysse et al. |
| 2003/0060818 A1 | 3/2003 | Kannenberg et al. |
| 2003/0065327 A1 | 4/2003 | Wellman et al. |
| 2003/0065358 A1 | 4/2003 | Frecker et al. |
| 2003/0069571 A1 | 4/2003 | Treat et al. |
| 2003/0109871 A1 | 6/2003 | Johnson et al. |
| 2003/0114845 A1 | 6/2003 | Paton et al. |
| 2003/0114848 A1 | 6/2003 | Cobb |
| 2003/0114851 A1 | 6/2003 | Truckai et al. |
| 2003/0125728 A1 | 7/2003 | Nezhat et al. |
| 2003/0125731 A1 | 7/2003 | Smith et al. |
| 2003/0125734 A1 | 7/2003 | Mollenauer |
| 2003/0139741 A1 | 7/2003 | Goble et al. |
| 2003/0181910 A1 | 9/2003 | Dycus et al. |
| 2003/0199863 A1 | 10/2003 | Swanson et al. |
| 2003/0199870 A1 | 10/2003 | Truckai et al. |
| 2003/0229344 A1 | 12/2003 | Dycus et al. |
| 2003/0236549 A1 | 12/2003 | Bonadio et al. |
| 2004/0006340 A1 | 1/2004 | Latterell et al. |
| 2004/0010289 A1 | 1/2004 | Biggs et al. |
| 2004/0068274 A1 | 4/2004 | Hooven |
| 2004/0068304 A1 | 4/2004 | Paton et al. |
| 2004/0073247 A1 | 4/2004 | Loshakove et al. |
| 2004/0082946 A1 | 4/2004 | Malis et al. |
| 2004/0092922 A1 | 5/2004 | Kadziauskas et al. |
| 2004/0122423 A1 | 6/2004 | Dycus et al. |
| 2004/0162557 A1 | 8/2004 | Tetzlaff et al. |
| 2004/0193148 A1 | 9/2004 | Wham et al. |
| 2004/0215127 A1 | 10/2004 | Kadziauskas et al. |
| 2004/0225288 A1 | 11/2004 | Buysse et al. |
| 2004/0250419 A1 | 12/2004 | Sremich et al. |
| 2005/0004563 A1 | 1/2005 | Racz et al. |
| 2005/0004564 A1 | 1/2005 | Wham et al. |
| 2005/0015125 A1 | 1/2005 | Mioduski et al. |
| 2005/0021027 A1 | 1/2005 | Shields et al. |
| 2005/0033282 A1 | 2/2005 | Hooven |
| 2005/0033352 A1 | 2/2005 | Zepf et al. |
| 2005/0080319 A1 | 4/2005 | Dinkler, II et al. |
| 2005/0090815 A1 | 4/2005 | Francischelli et al. |
| 2005/0096681 A1 | 5/2005 | Desinger et al. |
| 2005/0101951 A1 | 5/2005 | Wham et al. |
| 2005/0107785 A1 | 5/2005 | Dycus et al. |
| 2005/0113817 A1 | 5/2005 | Isaacson et al. |
| 2005/0113819 A1 | 5/2005 | Wham et al. |
| 2005/0124915 A1 | 6/2005 | Eggers et al. |
| 2005/0124987 A1 | 6/2005 | Goble |
| 2005/0137592 A1 | 6/2005 | Nguyen et al. |
| 2005/0149017 A1 | 7/2005 | Dycus |
| 2005/0159745 A1 | 7/2005 | Truckai et al. |
| 2005/0165444 A1 | 7/2005 | Hart et al. |
| 2005/0192568 A1 | 9/2005 | Truckai et al. |
| 2005/0203504 A1 | 9/2005 | Wham et al. |
| 2005/0234447 A1 | 10/2005 | Paton et al. |

(56) References Cited

U.S. PATENT DOCUMENTS

| | | |
|---|---|---|
| 2005/0245918 A1 | 11/2005 | Sliwa, Jr. et al. |
| 2005/0245922 A1 | 11/2005 | Goble |
| 2006/0020265 A1 | 1/2006 | Ryan |
| 2006/0041254 A1 | 2/2006 | Francischelli et al. |
| 2006/0052777 A1 | 3/2006 | Dumbauld |
| 2006/0079788 A1 | 4/2006 | Anderson et al. |
| 2006/0079878 A1 | 4/2006 | Houser |
| 2006/0129146 A1 | 6/2006 | Dycus et al. |
| 2006/0161190 A1 | 7/2006 | Gadberry et al. |
| 2006/0167450 A1 | 7/2006 | Johnson et al. |
| 2006/0173453 A1 | 8/2006 | Gruhl et al. |
| 2006/0217697 A1 | 9/2006 | Lau et al. |
| 2006/0217706 A1 | 9/2006 | Lau et al. |
| 2006/0217707 A1 | 9/2006 | Daniel et al. |
| 2006/0224152 A1 | 10/2006 | Behnke et al. |
| 2006/0224158 A1 | 10/2006 | Odom et al. |
| 2006/0247498 A1 | 11/2006 | Bonadio et al. |
| 2006/0271042 A1 | 11/2006 | Latterell et al. |
| 2007/0016185 A1 | 1/2007 | Tullis et al. |
| 2007/0043352 A1 | 2/2007 | Garrison et al. |
| 2007/0043353 A1 | 2/2007 | Dycus et al. |
| 2007/0062017 A1 | 3/2007 | Dycus et al. |
| 2007/0088202 A1 | 4/2007 | Albrecht et al. |
| 2007/0090788 A1 | 4/2007 | Hansford et al. |
| 2007/0093800 A1 | 4/2007 | Wham et al. |
| 2007/0123847 A1 | 5/2007 | Mihori |
| 2007/0135811 A1 | 6/2007 | Hooven |
| 2007/0142833 A1 | 6/2007 | Dycus et al. |
| 2007/0142834 A1 | 6/2007 | Dumbauld |
| 2007/0156139 A1 | 7/2007 | Schecter et al. |
| 2007/0156140 A1 | 7/2007 | Baily |
| 2007/0167941 A1 | 7/2007 | Hamel et al. |
| 2007/0173811 A1 | 7/2007 | Couture et al. |
| 2007/0173813 A1 | 7/2007 | Odom |
| 2007/0173814 A1 | 7/2007 | Hixson et al. |
| 2007/0179499 A1 | 8/2007 | Garrison |
| 2007/0191827 A1 | 8/2007 | Lischinsky et al. |
| 2007/0191828 A1 | 8/2007 | Houser et al. |
| 2007/0203481 A1 | 8/2007 | Gregg et al. |
| 2007/0213712 A1 | 9/2007 | Buysse et al. |
| 2007/0260242 A1 | 11/2007 | Dycus et al. |
| 2007/0276363 A1 | 11/2007 | Patton et al. |
| 2007/0282195 A1 | 12/2007 | Masini et al. |
| 2007/0282320 A1 | 12/2007 | Buysse et al. |
| 2007/0282332 A1 | 12/2007 | Witt et al. |
| 2007/0287997 A1 | 12/2007 | Tolmei |
| 2008/0009860 A1 | 1/2008 | Odom |
| 2008/0015563 A1 | 1/2008 | Hoey et al. |
| 2008/0015564 A1 | 1/2008 | Wham et al. |
| 2008/0015567 A1 | 1/2008 | Kimura |
| 2008/0030206 A1 | 2/2008 | Podhajsky et al. |
| 2008/0039831 A1 | 2/2008 | Odom et al. |
| 2008/0045947 A1 | 2/2008 | Johnson et al. |
| 2008/0058802 A1 | 3/2008 | Couture et al. |
| 2008/0082098 A1 | 4/2008 | Tanaka et al. |
| 2008/0091189 A1 | 4/2008 | Carlton |
| 2008/0114356 A1 | 5/2008 | Johnson et al. |
| 2008/0125772 A1 | 5/2008 | Stone et al. |
| 2008/0132893 A1 | 6/2008 | D+ Amelio et al. |
| 2008/0167651 A1 | 7/2008 | Tetzlaff et al. |
| 2008/0172048 A1 | 7/2008 | Martin et al. |
| 2008/0188848 A1 | 8/2008 | Deutmeyer et al. |
| 2008/0208246 A1 | 8/2008 | Livneh |
| 2008/0215050 A1 | 9/2008 | Bakos |
| 2008/0215051 A1 | 9/2008 | Buysse et al. |
| 2008/0221565 A1 | 9/2008 | Eder et al. |
| 2008/0228179 A1 | 9/2008 | Eder et al. |
| 2008/0294222 A1 | 11/2008 | Schecter |
| 2008/0300589 A1 | 12/2008 | Paul et al. |
| 2008/0300590 A1 | 12/2008 | Horne et al. |
| 2008/0300591 A1 | 12/2008 | Darian et al. |
| 2009/0012520 A1 | 1/2009 | Hixson et al. |
| 2009/0024126 A1 | 1/2009 | Artale et al. |
| 2009/0171352 A1 | 7/2009 | Sutter |
| 2009/0248007 A1 | 10/2009 | Falkenstein et al. |
| 2009/0275490 A1 | 11/2009 | Milne et al. |
| 2009/0275940 A1 | 11/2009 | Malackowski et al. |
| 2012/0010614 A1 | 1/2012 | Couture |
| 2012/0059371 A1 | 3/2012 | Anderson et al. |
| 2012/0083785 A1 | 4/2012 | Roy et al. |
| 2012/0136347 A1 | 5/2012 | Brustad et al. |
| 2012/0197243 A1 | 8/2012 | Sherman et al. |
| 2012/0215220 A1 | 8/2012 | Manzo et al. |
| 2013/0018411 A1 | 1/2013 | Collings et al. |
| 2013/0138101 A1 | 5/2013 | Kerr |
| 2013/0138102 A1 | 5/2013 | Twomey et al. |
| 2013/0197874 A1 | 8/2013 | Heckel |
| 2013/0267951 A1 | 10/2013 | Twomey |
| 2013/0274743 A1 | 10/2013 | Banfalvi |
| 2013/0296843 A1 | 11/2013 | Boudreux et al. |
| 2013/0345696 A1 | 12/2013 | Behnke, II et al. |
| 2014/0005658 A1 | 1/2014 | Rosenbegr |
| 2014/0088583 A1 | 3/2014 | Singh |
| 2014/0214019 A1 | 7/2014 | Baxter, III et al. |
| 2016/0310203 A1 | 10/2016 | Gaspredes et al. |
| 2016/0310204 A1* | 10/2016 | Mchenry ............ A61B 18/1233 |

FOREIGN PATENT DOCUMENTS

| | | |
|---|---|---|
| DE | 10 2005 044 918 A1 | 2/2007 |
| EP | 0 315 338 A1 | 5/1989 |
| EP | 0 538 984 A2 | 4/1993 |
| EP | 0 570 675 B1 | 11/1993 |
| EP | 0 598 202 B1 | 5/1994 |
| EP | 0 717 967 A2 | 6/1996 |
| EP | 0 737 447 A1 | 10/1996 |
| EP | 0 878 168 A1 | 11/1998 |
| EP | 1 054 637 B1 | 11/2000 |
| EP | 1 157 666 A1 | 11/2001 |
| EP | 1 500 378 A1 | 1/2005 |
| EP | 1 535 581 A2 | 6/2005 |
| EP | 1 545 361 B1 | 6/2005 |
| EP | 1 557 129 A1 | 7/2005 |
| EP | 1 634 539 A1 | 3/2006 |
| EP | 1 634 539 B1 | 3/2006 |
| EP | 1 665 995 A1 | 6/2006 |
| EP | 1 728 475 A2 | 12/2006 |
| EP | 1 810 628 A1 | 7/2007 |
| EP | 1 946 715 A1 | 7/2008 |
| EP | 2 106 762 A1 | 10/2009 |
| EP | 2 111 812 A2 | 10/2009 |
| EP | 2 156 802 A2 | 2/2010 |
| EP | 2 301 462 A1 | 3/2011 |
| EP | 2 340 792 A1 | 7/2011 |
| EP | 2 436 327 A1 | 4/2012 |
| EP | 2 436 330 A1 | 4/2012 |
| EP | 2 574 300 A1 | 4/2013 |
| EP | 2 712 568 A2 | 4/2014 |
| EP | 2 777 578 A1 | 9/2014 |
| EP | 3 369 392 A2 | 9/2018 |
| GB | 2 157 175 A | 10/1985 |
| GB | 2 462 453 A | 8/2008 |
| JP | 60-30946 A | 2/1994 |
| JP | 83-17935 A | 12/1996 |
| JP | 11-070123 A | 3/1999 |
| JP | 11-070124 A | 3/1999 |
| JP | 11-178833 A | 7/1999 |
| JP | 2000-254135 A | 9/2000 |
| JP | 2003-135481 A | 5/2003 |
| JP | 2003-164463 A | 6/2003 |
| JP | 2006-109945 A | 4/2006 |
| JP | 2006-167403 A | 6/2006 |
| JP | 2007-144201 A | 6/2007 |
| JP | 2007-195980 A | 8/2007 |
| JP | 2007-195985 A | 8/2007 |
| JP | 2008-043789 A | 2/2008 |
| JP | 2008-259864 A | 10/2008 |
| WO | WO 93/015662 A1 | 8/1993 |
| WO | WO 97/010764 A1 | 3/1997 |
| WO | WO 99/040857 A1 | 8/1999 |
| WO | WO 01/012090 A1 | 2/2001 |
| WO | WO 2004/030553 A1 | 4/2004 |
| WO | WO 2004/032776 A1 | 4/2004 |
| WO | WO 2004/032777 A1 | 4/2004 |

(56) References Cited

FOREIGN PATENT DOCUMENTS

| WO | WO 2004/082495 A1 | 9/2004 |
|---|---|---|
| WO | WO 2005/004735 A1 | 1/2005 |
| WO | WO 05/053785 A2 | 6/2005 |
| WO | WO 2006/119245 A2 | 11/2006 |
| WO | WO 2006/125558 A1 | 11/2006 |
| WO | WO 2007/044849 A1 | 4/2007 |
| WO | WO 2007/142601 A1 | 12/2007 |
| WO | WO 2008/147773 A1 | 12/2008 |
| WO | WO 2009/065140 A1 | 5/2009 |
| WO | WO 2012/110996 A2 | 8/2012 |
| WO | WO 2013/030349 A1 | 3/2013 |

OTHER PUBLICATIONS

International Preliminary Examining Authority/US, International Preliminaiy Report on Patentability for International Application No. PCT/US2019/059909, titled "Electrosurgical System," dated May 27, 2021, 15 pgs.
International Searching Authority/US, The International Search Report and the Written Opinion for International Application No. PCT/US2019/049768 titled "Electrosurgical Generator Verification System," dated Dec. 11, 2019, 19 pgs.
European Patent Office, Invitation to Pay Additional Fees for International Application No. PCT/US2019/049807, titled "Electrosurgical Generator Control System", mailed Dec. 19, 2019, 16 pgs.
International Searching Authority/US, The International Search Report and the Written Opinion for International Application No. PCT/US2019/059909 titled "Electrosurgical System," dated Apr. 28, 2020, 23 pgs.
European Patent Office, Extended European Search Report for European Patent No. 19198318.8, entitled, "Bipolar Electrosurgical Sealer and Divider," dated Dec. 17, 2019, 10 pgs.
International Searching Authority/US, The International Search Report and the Written Opinion for International Application No. PCT/US2019/049807 titled "Electrosurgical Generator Control System," dated Feb. 12, 2020, 20 pgs.
International Preliminary Examining Authority/US, International Preliminary Report on Patentability for International Application No. PCT/US2019/049768, titled "Electrosurgical Generator Verification System," dated Mar. 18, 2021, 13 pgs.
International Preliminary Examining Authority/US, International Preliminary Report on Patentability for International Application No. PCT/US2019/049807, titled "Electrosurgical Generator Control System," dated Mar. 18, 2021, 13 pgs.
Bertil Vallfors and Bjorn Bergdahl, Automatically controlled bipolar electrocoagulation—"COA-COMP", Neurosurg. Rev., 1984, pp. 187-190.
"New Products" Journal of Medical Engineering and Technology, vol. 19, No. 5 (Sep./Oct. 1995), pp. 189-190.
International Searching Authority/US, The International Search Report and the Written Opinion for International Application No. PCT/US09/39046 titled "Electrosurgical System," dated Jul. 27, 2009, 31 pgs.
International Preliminary Examining Authority/US, International Preliminary Report on Patentability for International Application No. PCT/US09/39046, titled "Electrosurgical System," dated Mar. 26, 2010, 18 pgs.
European Patent Office, European Search Report for European Application No. EP 10 19 2593, titled "Electrosurgical System," dated Mar. 21, 2011, 8 pgs.
European Patent Office, European Search Report for European Application No. EP 10 19 2614, titled "Electrosurgical System," dated Apr. 18, 2011, 7 pgs.
European Patent Office, Extended European Search Report for European Application No. EP 10 19 2580, dated Jul. 21, 2011, 6 pgs.
International Preliminary Examining Authority/US, International Preliminary Report on Patentability for International Application No. PCT/US09/39046, titled "Electrosurgical System," dated Jan. 17, 2012, 45 pgs.
European Patent Office, European Search Report for European Patent Application No. 12151288, dated Feb. 10, 2012, 8 pgs.
European Patent Office, The International Search Report and Written Opinion of the International Searching Authority for International Application No. PCT/US2011/054661, dated Mar. 6, 2012, 23 pgs.
European Patent Office, Supplementary European Search Report for European Patent Application No. 08755322, dated Apr. 18, 2012, 3 pgs.
European Patent Office, Supplementary European Search Report for European Patent Application No. 08755322, dated Jun. 6, 2012, 2 pgs.
European Patent Office, Partial European Search Report for European Patent Application No. 15151398.3, dated Jun. 22, 2015, 9 pgs.
U.S. Appl. No. 12/611,352, filed Nov. 3, 2009, titled Tissue Fusion/Welder Apparatus and Method, now U.S. Pat. No. 8,551,089 issued Oct. 8, 2013.
U.S. Appl. No. 12/183,970, filed Jul. 31, 2008, entitled Bipolar Electrosurgical Scissors, now U.S. Pat. No. 8,226,649 issued Jul. 24, 2012.
U.S. Appl. No. 12/416,128, filed Mar. 31, 2009, entitled Electrosurgical System, now U.S. Pat. No. 8,568,411 issued Oct. 29, 2013.
U.S. Appl. No. PCT/US09/39046, filed Mar. 31, 2009, entitled Electrosurgical System.
U.S. Appl. No. 12/416,668, filed Apr. 1, 2009, entitled Electrosurgical System, now U.S. Pat. No. 8,562,598 issued Oct. 22, 2013.
U.S. Appl. No. 12/416,695, filed Apr. 1, 2009, entitled Electrosurgical System, now U.S. Pat. No. 8,551,088 issued Oct. 8, 2013.
U.S. Appl. No. 12/416,765, filed Apr. 1, 2009, entitled Electrosurgical System, now U.S. Pat. No. 8,915,910 issued Dec. 23, 2014.
U.S. Appl. No. 12/416,751, filed Apr. 1, 2009, entitled Electrosurgical System, now U.S. Pat. No. 8,579,894 issued Nov. 12, 2013.
The International Bureau of WIPO, The International Preliminary Report on Patentability for International Application No. PCT/US2011/054661, entitled "Electrosurgical Instruments and Connections Thereto," dated Apr. 2, 2013, 10 pgs.
European Patent Office, European Search Report for European Application No. EP 13 17 4814.7, titled "Electrosurgical System," dated Sep. 30, 2013, 4 pgs.
European Patent Office, European Search Report for European Patent Application No. EP 14199708.0, entitled "Electrosurgical System," dated Jul. 10, 2015, 14 pgs.
International Searching Authority/US, The International Search Report and the Written Opinion for International Application No. PCT/US2015/031452, titled "Electrosurgical Fusion Device," dated Dec. 3, 2015, 27 pgs.
International Searching Authority/US, The International Search Report and the Written Opinion for International Application No. PCT/US2015/066473 titled "Bipolar Electrosurgical Sealer and Divider," dated Mar. 31, 2016, 13 pgs.
International Searching Authority/US, The International Search Report and the Written Opinion for International Application No. PCT/US2015/033546 titled "Electrosurgical Seal and Dissection Systems," dated Apr. 22, 2016, 31 pgs.
International Preliminary Examining Authority/US, International Preliminary Report on Patentability for International Application No. PCT/US2015/031452, titled "Electrosurgical System," dated Dec. 1, 2016, 21 pgs.
International Preliminary Examining Authority/US, International Preliminary Report on Patentability for International Application No. PCT/US2015/033546, titled "Electrosurgical Laparoscopic Sealer and Dissector," dated Dec. 15, 2016, 22 pgs.
International Preliminary Examining Authority/US, International Preliminary Report on Patentability for International Application No. PCT/US2015/0066473, titled "Bipolar Electrosurgical Sealer and Divider," dated Jul. 6, 2017, 10 pgs.
European Patent Office, Extended European Search Report for European Application No. EP 17207793.5, dated May 16, 2018, 9 pgs.

(56) References Cited

OTHER PUBLICATIONS

European Patent Office, Extended European Search Report for European Application No. EP 18165110.0, dated Jun. 13, 2018, 6 pgs.

* cited by examiner

ELECTROSURGICAL SYSTEM

CROSS-REFERENCE TO RELATED APPLICATIONS

This application claims priority to and benefit of U.S. Provisional Patent Application Ser. No. 62/768,782 entitled "Electrosurgical System" filed on Nov. 16, 2018, which is incorporated herein by reference in its entirety.

BACKGROUND

The present application relates generally to electrosurgical systems and methods. More particularly, the present application relates to electrosurgical generators and associated instruments for sealing and cutting tissue.

There are available electrosurgical devices or instruments that use electrical energy to perform certain surgical tasks. Typically, electrosurgical instruments are surgical instruments such as graspers, scissors, tweezers, blades, and/or needles that include one or more electrodes that are configured to be supplied with electrical energy from an electrosurgical generator. The electrical energy can be used to coagulate, fuse, or cut tissue.

Electrosurgical instruments typically fall within two classifications: monopolar and bipolar. In monopolar instruments, electrical energy is supplied to one or more electrodes on the instrument with high current density while a separate return electrode is electrically coupled to a patient. The separate return electrode is often designed to minimize current density. Monopolar electrosurgical instruments can be useful in certain procedures but can include a risk of certain types of issues such as electrical burns that may be partially attributable to the functioning of the return electrode.

In bipolar electrosurgical instruments, one or more electrodes are electrically coupled to a source of electrical energy of a first polarity. In addition, one or more other electrodes are electrically coupled to a source of electrical energy of a second polarity opposite the first polarity. Bipolar electrosurgical instruments, which operate without separate return electrodes, can deliver electrical signals to a focused tissue area with reduced risks compared to monopolar electrosurgical instruments.

Even with the relatively focused surgical effects of bipolar electrosurgical instruments surgical, however, outcomes are often highly dependent on surgeon skill. For example, thermal tissue damage and necrosis can occur in instances where electrical energy is delivered for a relatively long duration or where a relatively high-powered electrical signal is delivered even for a short duration. The rate at which a tissue will achieve the desired fusing, sealing, or cutting effect upon the application of electrical energy varies based on the tissue type and can also vary based on pressure applied to the tissue by an electrosurgical device. However, it can be difficult for a surgeon to assess how quickly a mass of combined tissue types grasped in an electrosurgical instrument will be sealed a desirable amount.

SUMMARY OF THE INVENTION

Disclosed herein are methods, devices, and systems for fusing or sealing tissue. In a first embodiment, a method for fusing or sealing tissue is described. The method begins by first applying a first amount of RF energy to an area of tissue. A desiccation level of the area of tissue affected by the first amount of RF energy is then determined. Based on the determined desiccation level, the amount of RF energy is reduced to a second amount. Subsequent to reducing to the second amount of RF energy, an increasing amount of RF energy is applied to the area of tissue until a third amount is reached. A rate by which the RF energy is added and the third amount is based on the determined desiccation level. The third amount of RF energy is applied to the area of tissue for a pre-determined period of time. Once the pre-determined period of time has elapsed, the application of the RF energy to the area of tissue is terminated.

In another embodiment, an electrosurgical generator used for fusing or sealing tissue is described. The electrosurgical generator includes a controller and an RF amplifier that generates a corresponding amount of RF energy based on the instructions provided by the controller. The controller first instructs the RF amplifier to apply a first amount of RF energy to an area of tissue. The controller then determines a desiccation level of the area of tissue affected by the first amount of RF energy. The controller then instructs the RF amplifier to first reduce the amount of RF energy to a second amount based on the determined desiccation level and subsequently increase an amount of RF energy being applied to the area to a third amount. A rate by which the RF energy is added and the third amount is based on the determined desiccation level. The controller instructs the RF amplifier to maintain the third amount of RF energy being applied to the area of tissue for a pre-determined period of time. Once the pre-determined period of time has elapsed, the controller instructs the RF amplifier to terminate the application of the RF energy to the area of tissue.

In another embodiment, a system for fusing or sealing tissue is described. The system includes an electrosurgical generator that generates RF energy and an electrosurgical instrument that fuses or seals an area of tissue. The electrosurgical instrument receives the RF energy from the electrosurgical generator in order to fuse or seal the area of tissue. The amount of RF energy that is generated and provided to the electrosurgical instrument to use in the fusing or sealing of the area of tissue is based on a determined desiccation level of the area of tissue.

BRIEF DESCRIPTION OF THE DRAWINGS

In order to describe the manner which, the above-recited and other advantages and features of the disclosure can be obtained, a more particular description of the principles briefly described above will be rendered by reference to specific embodiments that are illustrated in the appended drawings. Understanding that these drawings depict only embodiments of the disclosure and are not therefore to be considered to be limiting of its scope, the principles herein are described and explained with additional specificity and detail through the use of the accompanying drawings in which the reference numerals designate like parts throughout the figures thereof.

DETAILED DESCRIPTION OF THE INVENTION

Figure 1:
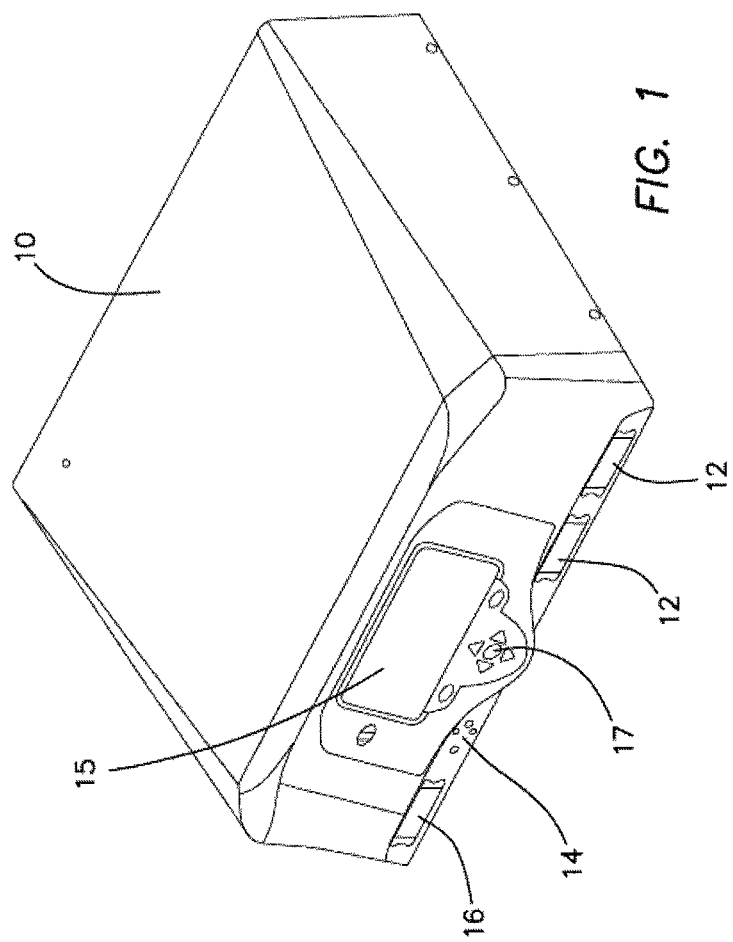
FIG. 1 is a perspective view of an electrosurgical system in accordance with various embodiments of the present invention.

In accordance with various embodiments, an electrosurgical instrument is provided that is configured to fuse and cut tissue. In various embodiments, the electrosurgical device or instrument includes a first jaw and a second jaw. The second jaw opposes the first jaw to facilitate the grasping of tissue between the first jaw and the second jaw. Both the first jaw and the second jaw include an electrode. The electrodes of the first jaw and the second jaw are arranged to seal tissue grasped between the first jaw and the second jaw using radio frequency (RF) energy.

In accordance with various embodiments, an electrosurgical system for sealing tissue is also provided. The electrosurgical system in various embodiments comprises an electrosurgical generator and an electrosurgical instrument or device. The electrosurgical generator includes an RF amplifier and a controller. The RF amplifier supplies RF energy through a removably coupled electrosurgical instrument configured to seal tissue with only RF energy. The controller and/or RF sense are arranged to monitor and/or measure the supplied RF energy and/or components thereof. In various embodiments, the controller signals the RF amplifier to adjust, e.g., increase, hold, decrease and/or stop, voltage of the supplied RF energy at predetermined points or conditions of a sealing cycle. In various embodiments, the controller signals the RF amplifier to halt the supplied RF energy or initiate termination of the supplied RF energy from the RF amplifier.

The various features and embodiments provided throughout can be used alone, or in combination with other features and/or embodiments other than as expressly described and although specific combinations of embodiments and features or aspects of various embodiments may not be explicitly described such combinations however are contemplated and within the scope of the present inventions. Many of the attendant features of the present inventions will be more readily appreciated as the same becomes better understood by reference to the foregoing and following description and considered in connection with the accompanying drawings.

Generally, an electrosurgical system is provided that includes an electrosurgical generator and a removably coupled electrosurgical instrument that are configured to optimally seal or fuse tissue. The RF energy is supplied by the electrosurgical generator that is arranged to provide the appropriate RF energy to seal the tissue. The electrosurgical generator, in accordance with various embodiments, determines the appropriate RF energy and the appropriate manner to deliver the RF energy for the particular connected electrosurgical instrument, the particular tissue in contact with the electrosurgical instrument, and/or a particular surgical procedure being performed. Operationally, RF sealing or fusing of tissue between the jaws is provided to decrease sealing time and/or thermal spread.

In accordance with various embodiments, the electrosurgical system comprises a dynamic pulse system arranged to control and shut off RF energy delivery that results in an optimal balance of hemostasis reliability, seal time, and tissue adherence for a wide range of tissues. In various embodiments, the electrosurgical system comprises a double or repeat seal system arranged to reduce the application of RF energy for multiple activations to reduce eschar (sealed tissue debris) buildup, tissue adherence, and thermal spread for tissue that is already sealed.

Figure 2:
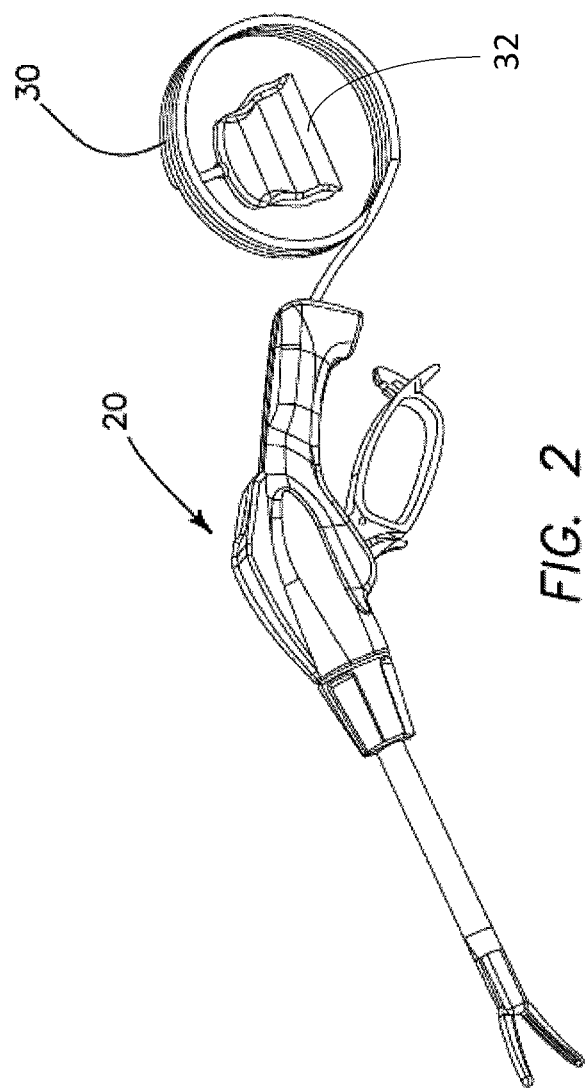
FIG. 2 and FIG. 3 are perspective views of an electrosurgical instrument in accordance with various embodiments of the present invention.

Referring to both FIG. 1 and FIG. 2, an exemplary embodiment of the electrosurgical system is illustrated. The electrosurgical system includes an electrosurgical generator 10 (as illustrated in FIG. 1) and a removably connectable electrosurgical instrument 20 (as illustrated in FIG. 2). The electrosurgical instrument 20 can be electrically coupled to the electrosurgical generator 10 via a cabled connection 30 having an adaptor 32 configured to connect to a tool or device port 12 on the electrosurgical generator 10. The electrosurgical instrument 20 may include audio, tactile and/or visual indicators to apprise a user of a particular predetermined status of the electrosurgical instrument 20 such as a start and/or end of a fusion or cut operation. In other embodiments, the electrosurgical instrument 20 can be reusable and/or connectable to another electrosurgical generator for another surgical procedure. In some embodiments, a manual controller such as a hand or foot switch can be connectable to the electrosurgical generator 10 and/or electrosurgical instrument 20 to allow predetermined selective control of the electrosurgical instrument 20 such as to commence a fusion or cut operation.

In accordance with various embodiments, the electrosurgical generator 10 is configured to generate radio frequency (RF) electrosurgical energy and to receive data or information from the electrosurgical instrument 20 electrically coupled to the electrosurgical generator 10. The electrosurgical generator 10, in one embodiment, outputs RF energy (e.g., 375VA, 150V, 5 A at 350 kHz) and in one embodiment is configured to measure current and/or voltage of the RF energy and/or to calculate power of the RF energy or a phase angle or difference between RF output voltage and RF output current during activation or supply of the RF energy. The electrosurgical generator 10 regulates voltage, current and/or power and monitors the RF energy output (e.g., voltage, current, power and/or phase). In one embodiment, the electrosurgical generator 10 stops the RF energy output under predefined conditions such as when a device switch is de-asserted (e.g., fuse button released), a time value is met, and/or active phase angle, current, voltage or power and/or changes thereto is greater than, less than or equal to a stop value, threshold or condition and/or changes thereto.

As illustrated in FIG. 1, the electrosurgical generator 10 comprises at least one advanced bipolar tool port 12, a standard bipolar tool port 16, and an electrical power port 14. In other embodiments, electrosurgical units can comprise different numbers of ports. For example, in some embodiments, an electrosurgical generator 10 can comprise more or fewer than two advanced bipolar tool ports, more or fewer than the standard bipolar tool port, and more or fewer than the power port. In one embodiment, the electrosurgical generator 10 comprises only two advanced bipolar tool ports.

In accordance with various embodiments, each advanced bipolar tool port 12 is configured to be coupled to an advanced electrosurgical instrument having an attached or integrated memory module. The standard bipolar tool port 16 is configured to receive a non-specialized bipolar electrosurgical tool that differs from the advanced bipolar electrosurgical instrument connectable to the advanced bipolar tool port 12. The electrical power port 14 is configured to receive or be connected to a direct current (DC) accessory device that differs from the non-specialized bipolar electrosurgical tool and the advanced electrosurgical instrument. The electrical power port 14 is configured to supply direct current voltage. For example, in some embodiments, the electrical power port 14 can provide approximately 12 Volts DC. The electrical power port 14 can be configured to power a surgical accessory, such as a respirator, pump, light, or another surgical accessory. Thus, in addition to replacing the electrosurgical generator 10 for standard or non-specialized bipolar tools, the electrosurgical generator 10 can also replace a surgical accessory power supply. In some embodiments, replacing presently-existing generators and power supplies with the electrosurgical generator 10 can reduce the amount of storage space required on storage racks cards or shelves and reduce the number of main power cords required in a surgical workspace.

In accordance with various embodiments, the electrosurgical generator 10 can comprise a display 15. The display 15 can be configured to indicate the status of the electrosurgical system including, among other information, the status of the one or more electrosurgical instruments and/or accessories, connectors or connections thereto.

The electrosurgical generator 10 in accordance with various embodiments can comprise a user interface, such as a plurality of buttons 17. The plurality of buttons 17 can allow user interaction (e.g., receiving user input) with the electrosurgical generator 10 such as, for example, requesting an increase or decrease in the electrical energy supplied to one or more electrosurgical instruments coupled to the electrosurgical generator 10. In other embodiments, the display 15 can be a touch screen display thus integrating data display and user interface functionalities. In one embodiment, the electrosurgical tool or instrument 20 can further comprise of one or more memory modules. In some embodiments, the memory comprises operational data concerning the electrosurgical instrument and/or other instruments. For example, in some embodiments, the operational data may include information regarding electrode configuration/reconfiguration, the electrosurgical instrument uses, operational time, voltage, power, phase and/or current settings, and/or particular operational states, conditions, scripts, processes or procedures. In one embodiment, the electrosurgical generator 10 can initiate reads and/or writes to the memory module.

In accordance with various embodiments, the electrosurgical generator 10 provides the capability to read the phase difference or phase angle between the voltage and current of the RF energy sent through the connected electrosurgical instrument 20 while RF energy is active. While tissue is being fused, phase readings are used to detect different states during the fuse or seal and cut process.

The electrosurgical generator 10 in accordance with various embodiments monitors, measures or calculates current, power, impedance or phase of the RF output, but does not control current, power, impedance or phase. The electrosurgical generator 10 regulates voltage and can also adjust voltage. Electrosurgical power delivered is a function of applied voltage, current, and tissue impedance. The electrosurgical generator 10, through the regulation of voltage, can affect the electrosurgical power, RF output, or energy being delivered. Power reactions are caused by the power interacting with the tissue or the state of the tissue without any control by a generator other than by the generator supplying power.

Once the electrosurgical generator 10 starts to deliver electrosurgical power, the electrosurgical generator 10 continues to do so continuously, e.g., for 150 ms, until a fault occurs or until a specific parameter is reached. In one example, the jaws of the electrosurgical instrument can be opened and thus compression relieved at any time before, during, and after the application of electrosurgical power. The electrosurgical generator 10, in one embodiment, also does not pause or wait a particular duration or a predetermined time delay to commence termination of the electrosurgical energy.

Figure 3:
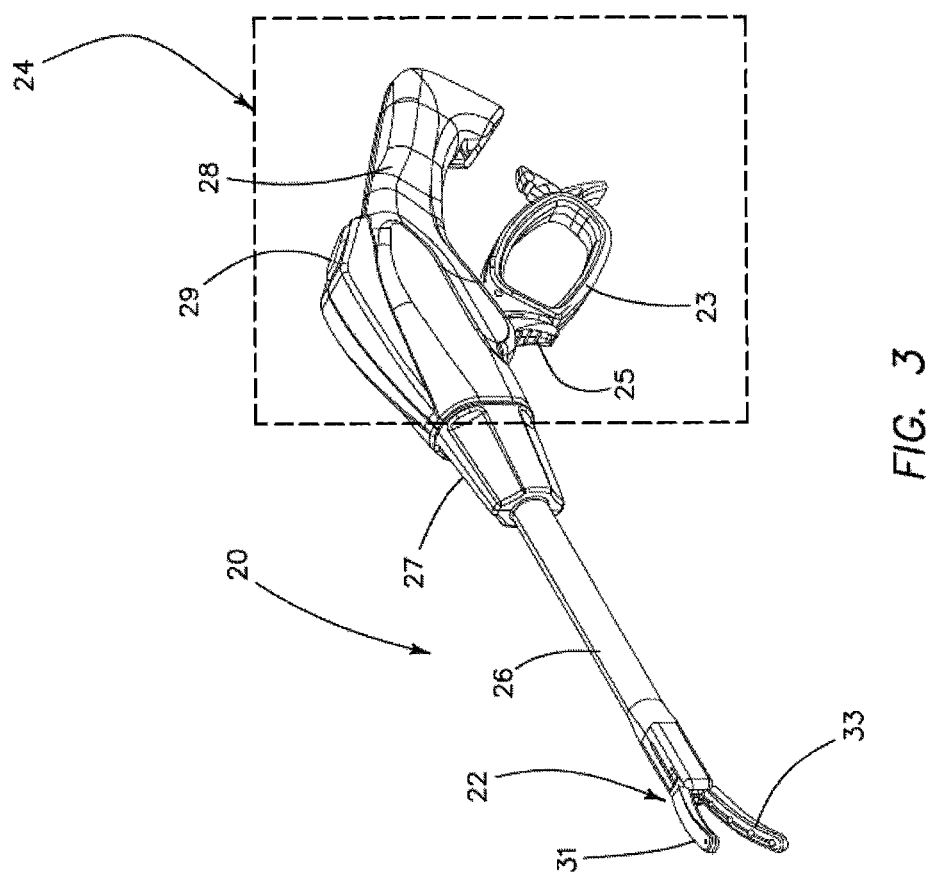

With additional reference to FIG. 3, in accordance with various embodiments, a bipolar electrosurgical instrument 20 is provided. In the illustrated embodiment, the bipolar electrosurgical instrument 20 includes an actuator 24 coupled to an elongate rotatable shaft 26. The elongate rotatable shaft 26 has a proximal end and a distal end defining a central longitudinal axis therebetween. At the distal end of the elongate rotatable shaft 26 are jaws 22 and at the proximal end is the actuator 24. In one embodiment, the actuator 24 is a pistol-grip like handle.

The actuator 24 includes a movable handle 23 and a stationary handle or housing 28. The movable handle 23 is coupled and movable relative to the stationary housing 28. In accordance with various embodiments, the movable handle 23 is slidably and pivotally coupled to the stationary housing 28. In operation, the movable handle 23 is manipulated by a user, e.g., a surgeon, to actuate the jaws, for example, selectively opening and closing the jaws 22.

In accordance with various embodiments, the actuator 24 includes a latch mechanism to maintain the movable handle 23 in a second position with respect to the stationary housing 28. In various embodiments, the movable handle 23 comprises a latch arm which engages a matching latch contained within the stationary handle or housing 28 for holding the movable handle 23 at a second or closed position. The actuator 24 in various embodiments also comprises a wire harness that includes insulated individual electrical wires or leads contained within a single sheath. The wire harness can exit the stationary housing 28 at a lower surface thereof and form part of the cabled connection 30 (as illustrated in FIG. 2). The wires within the harness can provide electrical communication between the electrosurgical instrument 20 and the electrosurgical generator 10 and/or accessories thereof.

In various embodiments, a switch is connected to a user manipulated activation button 29 and is activated when the activation button 29 is depressed. In one aspect, once activated, the switch completes a circuit by electrically coupling at least two leads together. As such, an electrical path is then established from an electrosurgical generator 10 to the actuator 24 to supply RF energy to the electrosurgical instrument 20. In various embodiments, the electrosurgical instrument 20 comprises a translatable mechanical cutting blade that can be coupled to a blade actuator such as a blade lever or trigger 25 of the actuator 24. The mechanical cutting blade is actuated by the blade trigger 25 to divide the tissue between the jaws 22.

In one embodiment, the actuator 24 includes an elongate rotatable shaft 26 assembly that includes a rotation knob 27 which is disposed on an outer cover tube of the elongate rotatable shaft 26. The rotation knob 27 allows a surgeon to rotate the elongate rotatable shaft 26 of the electrosurgical instrument 20 while gripping the actuator 24. In accordance with various embodiments, the elongate rotatable shaft 26 comprises an actuation tube coupling the jaws 22 with the actuator 24.

Attached to the distal end of the elongate rotatable shaft 26 are jaws 22 that comprise a first or upper jaw 31 and a second or lower jaw 33. In one embodiment, a jaw pivot pin pivotally couples the first jaw 31 and the second jaw 33 and allows the first jaw 31 to be movable and pivot relative to the second jaw 33. In various embodiments, one jaw is fixed with respect to the elongate rotatable shaft 26 such that the opposing jaw pivots with respect to the fixed jaw between an open and a closed position. In other embodiments, both the first jaw 31 and the second jaw 33 can be pivotally coupled to the elongate rotatable shaft 26 such that both the first jaw 31 and the second jaw 33 can pivot with respect to each other.

The first or upper jaw 31 includes an electrode plate or pad. Similarly, the second or lower jaw 33 also includes an electrode plate or pad. The electrode of the first or upper jaw 31 and the electrode of the second or lower jaw 33 are electrically coupled to the electrosurgical generator 10 via wires and connectors to supply RF energy to tissue grasped between the electrodes of the first jaw 31 and the second jaw 33. The electrodes, as such, are arranged to have opposing polarity and to transmit the RF energy therebetween. The first or upper jaw 31 in various embodiments also includes an upper jaw support with an assembly spacer positioned between the upper jaw support and the electrode. The first or upper jaw 31 also includes an overmold or is overmolded. The second or lower jaw 33 can also include a lower jaw support and the electrode. In the illustrated embodiment, the electrode is integrated or incorporated in the lower jaw support and thus the lower jaw support and the electrode form a monolithic structure and electrical connection. A blade channel extends longitudinally along the length of the first or upper jaw 31, the second or lower jaw 33, or both through which the blade operationally traverses. Surrounding a portion of the blade channel are one or more conductive posts. The conductive posts assist in immobilizing the tissue to be cut. The conductive posts also assist in ensuring the tissue being cut adjacent or proximate to the blade channel is fused as the conductive posts also participate in the transmission of RF energy to the tissue grasped between the jaws 22. The second or lower jaw 33 can also include an overmold or is overmolded.

In accordance with various embodiments, the electrodes have a generally planar sealing surface arranged to contact and compress tissue captured between the jaws 22. The electrodes of the first or upper jaw 31 and second or lower jaw 33 in various embodiments have a seal surface in which the width of the seal surface is uniform, constant, or remains unchanged throughout.

In various embodiments, the jaws 22 are curved to increase visualization and mobility of the jaws 22 at the targeted surgical site and during the surgical procedure. The jaws 22 have a proximal elongate portion that is denoted or aligned with straight lines and a curved distal portion denoting or defining a curve that is connected to the straight lines. In various embodiments, the proximal most portion of the proximal elongate portion has or delimits a diameter that equals or does not exceed a maximum outer diameter of the jaws 22 or elongate rotatable shaft 26. The jaws 22 in various embodiments have a maximum outer diameter in which the proximal most portion of the jaw 22 and the distal most portion of the jaws 22 remains within the maximum outer diameter. The curved distal potion has or delimits a diameter that is smaller than the maximum outer diameter and the diameter of the proximal most portion of the proximal elongate portion. In various embodiments, the jaw 22 has a deeper inner curve cut-out than the outer curve and in various embodiments the tip of the jaws 22 are tapered for blunt dissection. The jaws 22 include a blade channel having an proximal elongate channel curving to a distal curved channel in which the proximal elongate channel is parallel and offset to the longitudinal axis of the elongate rotatable shaft 26 of the electrosurgical instrument 20. As such, visibility and mobility at the jaws 22 are maintained or enhanced without increasing jaw dimensions that may further reduce the surgical working area or require larger access devices or incisions into the patient's body.

In some embodiments, electrode geometry of the conductive pads of the jaw assembly ensures that the sealing area or surface completely encloses the distal portion of the cutting path. In accordance with various embodiments, the dimensions of the jaw surfaces are such that it is appropriately proportioned with regards to the optimal pressure applied to the tissue between the jaws 22 for the potential force the force mechanism can create. Its surface area is also electrically significant with regards to the surface area contacting the tissue. This proportion of the surface area and the thickness of the tissue have been optimized with respect to its relationship to the electrical relative properties of the tissue.

In various embodiments, the second or lower jaw 33 and an associated conductive pad have an upper outer surface arranged to be in contact with tissue. The upper surfaces are angled or sloped and mirror images of each other with such positioning or orientation facilitating focused current densities and securement of tissue. In various embodiments, the second or lower jaw 33 is made of stainless steel and is as rigid as or more rigid than the conductive pad. In various embodiments, the second or lower jaw 33 comprises rigid insulators made of a non-conductive material and are as rigid as or more rigid than the second or lower jaw 33 or the conductive pad. In various embodiments, the second or lower jaw 33 and the conductive pad are made of the same material.

Figure 4:
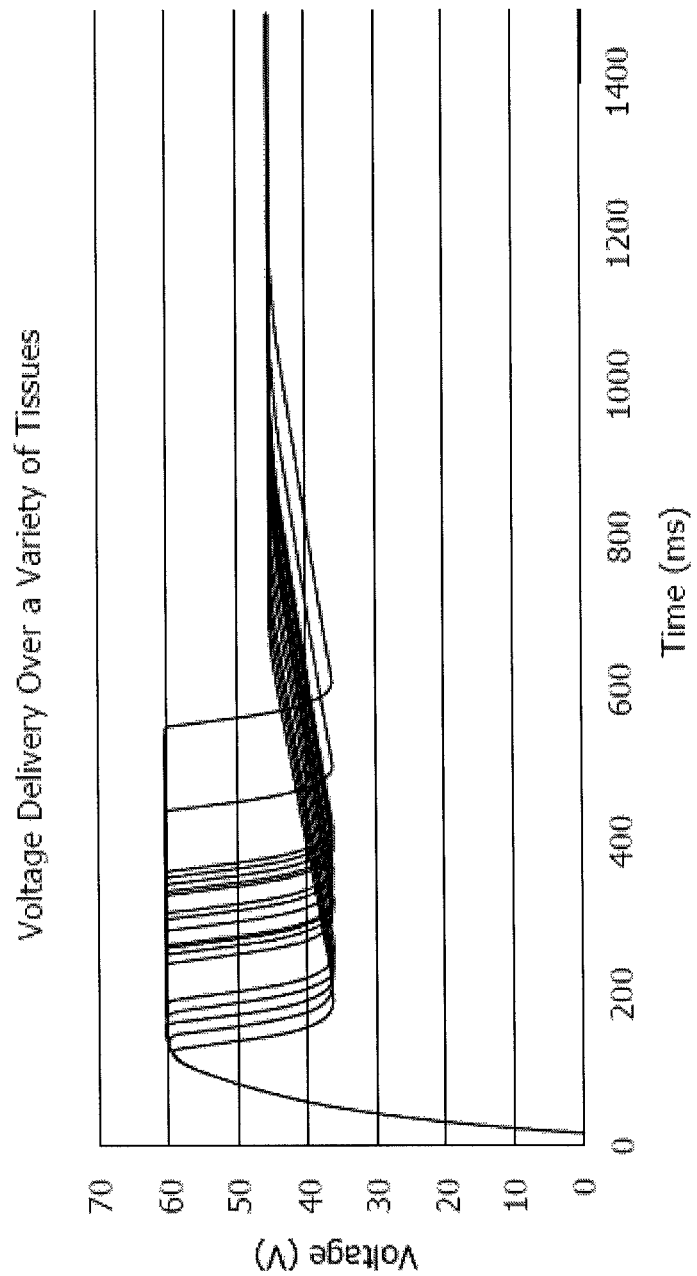
FIG. 4 to FIG. 7 are graphical representations of samples of experimental data for a sealing process or aspects thereof with an electrosurgical system in accordance with various embodiments of the present invention.

In accordance with various embodiments, the RF energy control process or system supplies RF energy and controls the supplied RF energy to seal or fuse tissue. At the beginning of a seal cycle, the system is arranged to apply RF energy having a quickly increasing voltage. As such, the system provides RF energy having voltage that increases over a minimal time period resulting in the supplied RF energy with a voltage profile having a steep slope or change rate. In accordance with various embodiments, the system seeks to continue to increase voltage of the RF energy to identify or determine an RF output peak condition. In accordance with various embodiments, the RF output peak condition is denoted by a maximum current or power value resulting from the increasing voltage of the supplied RF energy. In various embodiments, the system seeks to increase voltage of the supplied RF energy up to and/or equal to this RF output peak condition. However, determining this RF output peak condition or point can vary based on tissue type and/or tissue volume in contact with the electrode or electrodes of the electrosurgical instrument. As such, the high voltage ramp or pulse provided by the system has a duration that is variable based on the tissue in contact with the instrument rather than a static, fixed, or predefined value, as exemplified in FIG. 4. Similarly, electrode size and electrode contact relative to the tissue can further cause variations in this RF output peak condition. As such, determination of the RF output peak condition can be difficult.

Figure 5:
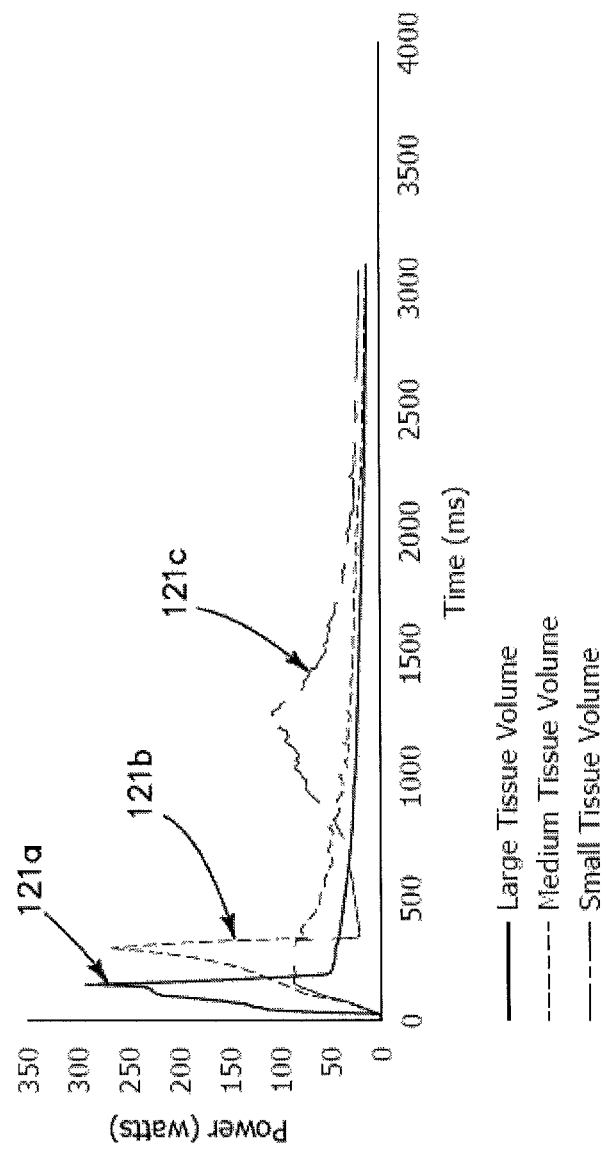

With the system seeking to reach this varying RF output peak condition, the amount of time the system or electrosurgical generator supplies RF energy can also vary. For example, as shown in FIG. 5, the peak conditions 121 occur at different times with tissue of different volumes. For example, tissue with smaller volumes may experience their respective peak conditions much earlier within a seal cycle compared to tissue that may have a much larger volume (e.g., as late as 1250 ms into a seal cycle). As such, the peak condition in various embodiments generally happens later for thicker tissue, as thicker tissues may take longer to heat up. Furthermore, the height of the peak can be determined by the surface area of the tissue. Tissues with larger surface areas may have higher peak values due to having more tissue being or acting as electrically parallel resistance. In various embodiments, however, the amount of time for quickly increasing the voltage of the RF energy being applied to the tissue is limited to a set maximum time threshold or limit and as a result avoids applying the RF energy longer than necessary. Setting a static time without seeking to reach the RF output peak condition however can lead to applying the RF energy longer than necessary, particularly for small tissue volumes. Furthermore, the use of static times can also present the situation where applying RF energy may not be long enough, particularly for large tissue volumes.

Accordingly, in accordance with various embodiments, providing a dynamic voltage ramp balances system performance on each end and allows for a close-to-ideal or optimal RF energy dosage initially or early and ultimately resulting in optimal tissue sealing. Rapidly achieving this RF output peak condition optimizes overall sealing of tissue and reduces time to seal without losing or reducing tissue integrity. In accordance with various embodiments, the electrosurgical generator initially adjusts the voltage of the RF energy to be relatively high (e.g., 40% or greater than the maximum voltage) and increases the voltage of the RF energy quickly (e.g., at a rate 10 volts per millisecond) to provide this dynamic voltage ramp or pulse to achieve the RF output peak condition.

Using a dynamic ramp ensures any tissue, regardless of volume, for example, is brought to the same RF output peak condition or water vaporization point quickly. As such, the likelihood of failing to reach or maintain the water vaporization point of the tissue (under-pulsing) is reduced. By reducing the likelihood of under-pulsing, the average RF delivery after the pulse can be shortened in time or lowered in power without affecting seal quality. Furthermore, the focus or attention of the system can be directed to removing water from the tissue efficiently, rather than variability associated with heating tissue.

As previously noted, determining when the RF output peak condition occurs is difficult, particularly in real-time. Noise or similar fluctuations or imprecision in measurement of the RF output may obscure or delay the determination of the RF output peak condition. Smoothing or filtering out such imprecisions, in various embodiments, can assist in enhancing detection or determination of the RF output peak condition. Delays in filter processing and the like in various embodiments may however also delay the determination of the RF output peak condition. Delays in identifying the determination of the RF output peak condition can cause the system to over-pulse the tissue.

In accordance with various embodiments, to avoid or reduce this delay in identifying the RF output peak condition or a potential over-pulse of the tissue, the system can provide a break system. The break system utilizes a break value defined based on a predicted maximum value or window representing the RF output peak condition. In various embodiments, the break value is as a percentage of the predicted maximum and/or a static threshold or gap, e.g., 400 mA or 30 W, below or within a predicted maximum value or window. The system monitors the RF output, e.g., the current and/or power, and the break system ensures that the monitored current and/or power reaches this break value before the voltage is adjusted, e.g., dropped, to ensure the RF output peak condition is quickly and accurately identified, thereby balancing both interests. It is however recognized that the lower or greater offset of the break value below the predicted maximum, the longer the specifically high voltage of the RF output is applied, e.g., over-pulse, but the less likely the system is to prematurely halt or drop the voltage of the RF output, e.g., under-pulse, due to for example triggering on noise.

In various embodiments, the system records or stores a predicted maximum value and looks for the next monitored value to exceed the stored predicted maximum value. When this occurs, the monitored value is stored as the "new" maximum value. In various embodiments, the system monitors or records the RF output at set intervals, such as every 50 ms, and compares the interested value of the RF output against the stored predicted maximum value to determine if a new maximum has occurred.

In accordance with various embodiments, the system utilizes a series of states with exit conditions set at regular intervals. As RF energy is applied and the value of interest changes, e.g., power and/or current increases, states are progressed through or cascaded. By increasing the number of states, the resolution of the cascade increase. However, depending on the resolution of the cascade, some accuracy can be lost in determining the RF output peak condition. A cascade or similar progression of states however is computationally less intensive and does not require or minimize the use of variables.

In accordance with various embodiments, the break value or range is calculated from a predicted maximum value by multiplying the predicted value by a percentage, e.g., 80%. Higher predicted maximums could require a larger drop in the interested value (e.g., current or power) to trigger or to identify the RF output peak condition. A break value or range in various embodiments is calculated from the predicted maximum value and subtracting a static offset (e.g., 400 mA or 30 W). Depending on the predicted maximum, this can be result in smaller or larger values than a percentage calculation but can be useful when the amplitude of noise or similar imprecision in the system is known, as the offset can be set to account for the imprecision (e.g., set higher than the amplitude of the noise). To ensure that a peak is detectable, the interested value (e.g., current or power) can be checked against the break value—in some scenarios the interested value (e.g., current or power) must reach at least the break value prior to any adjustments to the voltage to ensure that a peak can be identified. In various embodiments, the system provides a combination of the offset and percentage acting in parallel or serially and/or varying the order to enhance the identification or determination of the RF output peak condition to, for example, account for known imprecisions or when the predicted maximum value reaches a specific threshold where a larger drop in the interested value to trigger is not desired.

In various embodiments, the system monitors a rate of change of the interested value (e.g., current and/or power) to determine or to anticipate the RF output condition. As such, the system monitors the derivative or rate of the interested value and a change (e.g., a reduction in the change or rate) to identify the RF output peak condition or an indication that the RF output peak condition is near or close to occurring.

In various embodiments, the system is arranged to adjust the current of the RF output to determine the RF output peak condition. In particular, the system, e.g., the RF amplifier of the generator, gradually ramps up current of the supplied RF energy and the generator is placed in current regulation. When a current regulation value exceeds the tissue's ability to take more current, the system will no longer be current regulated, resulting in a sharp increase in voltage as the system switches regulation. This voltage condition is thus used as an indication or determination of the RF output peak condition. As such, this system regulation can forgo the use of a predicted maximum value of interest being stored or utilized as provided in the percentage or offset systems or processes.

In various embodiments, if errors or an unexpected result occurs, the system terminates the process, e.g., the supplying of the RF energy. In various embodiments, such errors comprise a short detection error or open detection error. In one embodiment, a short detection error is determined by the electrosurgical generator when a measured phase angle of the supplied RF energy by the electrosurgical generator equals or exceeds a predetermined value, e.g., sixty degrees. In one embodiment, an open detection error is determined by the electrosurgical generator when a measured current of the supplied RF energy equals or is below a predetermined value, e.g., 100 milliamps, and/or a measured voltage of the supplied RF energy equals or exceeds a predetermined value, e.g., 50 volts. Completion of the control process without errors indicates a successful tissue seal. A successful tissue seal in accordance with various embodiments is recognized as the tissue seal being able to withstand a predetermined range of burst pressures or a specific threshold pressure.

In accordance with various embodiments, it has been identified that tissue seal formation is dependent on denaturization and cross linkage of the native collagen present in vasculature extra cellular matrix which starts at about 60° C. The strength of this matrix is highly dependent on desiccation (or removal of moisture) at the seal site via vaporization of the water present in the sealed tissue. Additionally, at a temperature of at least 80° C., bonds between the denatured collagen and other living tissues can be created. Furthermore, that collagen degrades in response to duration under elevated temperature rather than the peak temperature of exposure. As such, exposing tissue to high temperature conditions (e.g., 100° C.) for the duration of a relatively short seal cycle does not impact the structure of the collagen but allows for the vaporization of water. The total time to seal tissue, in accordance with various embodiments, is reliant on heating the structure to the high temperature, e.g., 100° C., to vaporize water such that the denatured collagen crosslinks and bonds to tissue and to limit collagen-water hydrogen bonding. To optimize seal time, it was therefore found to be desirable to achieve 100° C. within the grasped tissue as quickly as possible to begin the desiccation process.

As such, in accordance with various embodiments, after RF energy has been initiated and/or various device checks are performed, the electrosurgical generator employs through the supplied RF energy a dynamic voltage ramp. Once the dynamic voltage ramp is complete, the system reduces the voltage to a predetermined level and slowly ramps up the voltage of the supplied RF energy. While the ramp occurs, sufficient amount of power is applied to the tissue to maintain a temperature sufficient for desiccation. This allows for continuous vaporization at a rate that does not cause seal structural failures and enhances vessel sealing performance.

In an embodiment, the application of high voltage levels may cause the sealed tissue to adhere to the active electrodes. As such, termination of the voltage ramp at a lower peak voltage and holding that voltage output constant at the end allows for continued energy application while reducing the potential for tissue adherence to the active electrodes. Determination of when to terminate the voltage ramp, in accordance with various embodiments, is conducted by monitoring the phase and current of the supplied RF energy. As the tissue desiccates, the phase will become more capacitive and will draw less current. By terminating the voltage ramp at a fixed current value as it falls and when the phase is capacitive, the desiccation level of the tissue can be categorized. This variable voltage set point allows the seal cycle to adjust the energy application based on electrical and structural differences in tissues being sealed.

In various embodiments, in order to achieve the appropriate tissue effect, the phase angle, current, and/or power of the applied RF energy are measured, calculated, and/or monitored. FIG. 4 to FIG. 7 provide graphical representations of exemplary seal cycles in accordance with various embodiments. As illustrated in FIG. 7, voltage 111a is shown relative to other RF output readings or indicators such as power 111b, impedance 111c, energy 111d, current 111e, and phase 111f. Additionally, although shown in FIG. 4 to FIG. 7, in various embodiments, the electrosurgical generator can be configured to not measure or not calculate one or more of the indicators or readings (e.g., impedance) to reduce operational and power costs and consumptions, and/or reduce the number of parts of the electrosurgical generator. The additional information or readings are generally provided or shown for contextual purposes. Additionally, in various embodiments, impedance or temperature readings may not be used or may not be measured being that such readings may be imprecise or impractical.

Figure 6:
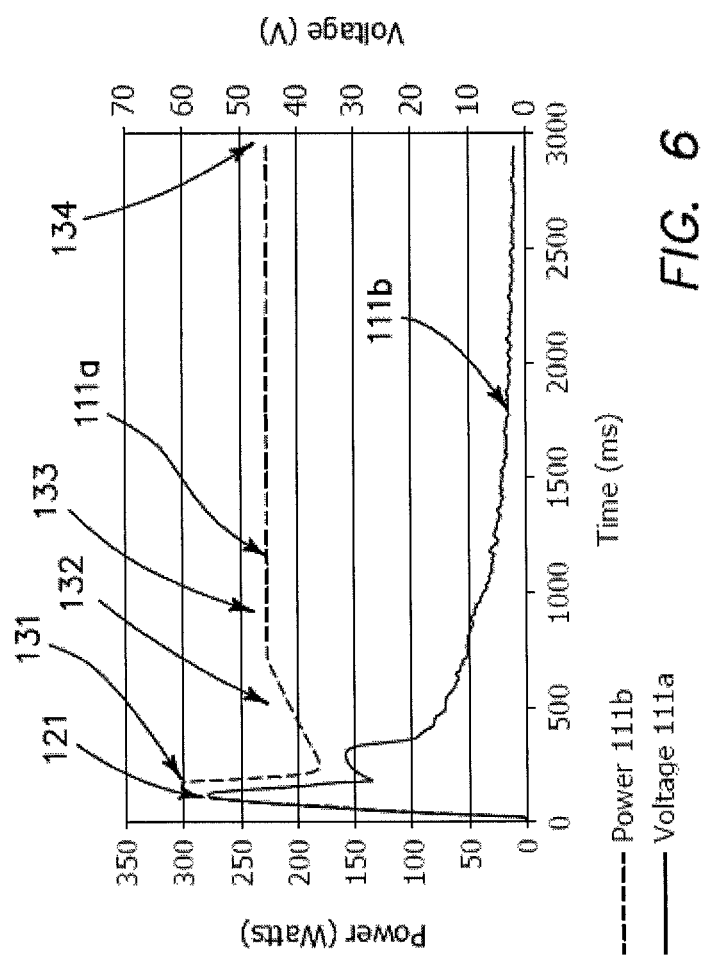
Figure 7:
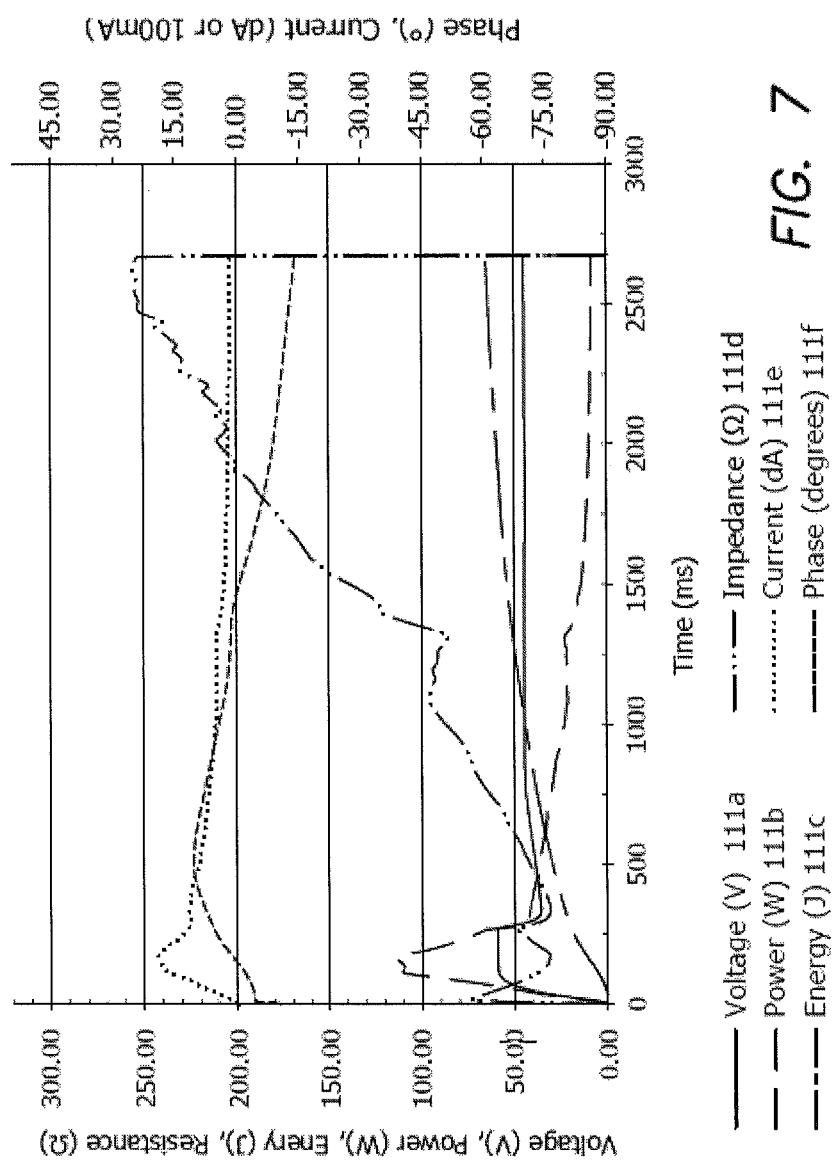

As shown in FIG. 7, the voltage of the RF output 111a is increased in the initial moments of the seal cycle and for a period relatively short compared to the total seal time to generate the voltage ramp or pulse of RF energy 131 (illustrated in FIG. 6). In accordance with various embodiments, the system seeks to determine or reach the RF output peak condition 121. Subsequently after reaching the RF output peak condition 121, the voltage of the RF energy is reduced and ramped up, slowly, relative to the voltage pulse. In various embodiments, the slow voltage ramp 132 by the system seeks to maintain the tissue between the jaws close to at least 100° C. and thereby control the boiling rate of water in the tissue. In accordance with various embodiments, in order to achieve the appropriate tissue effect of sealing the tissue, the phase angle, current, and power of the applied RF energy are monitored. Voltage of the RF energy is then held constant 133 to reduce the potential for tissue adherence. At seal completion (e.g., within a predetermined time frame or period according to the system), the RF energy supplied by the system is terminated or the RF energy supply is halted, disrupted, or stopped 134. In various embodiments, the voltage ramp of the RF energy is terminated and after a predefined time period according to the system, the RF energy supplied by the system is terminated or the RF energy supply is halted, disrupted, or stopped.

In various embodiments, the system identifies unintended current draw provided, for example, in some tissue bundles that draw the maximum current or power that can be supplied by the generator. While the system is under such a current condition, the supply of RF energy required to seal the tissue may not be sufficient or be efficiently supplied by the system. In various embodiments, to handle such a condition, the system determines if the current of the RF energy output is greater than 90% of the allowable maximum current, e.g., 4500 mA. If so, the system waits or delays further to ensure that the current has sufficiently dropped thereby indicating that sufficient desiccation of the tissue has occurred. If, after such a delay, the current has not sufficiently dropped, an error is indicated and/or the RF energy being supplied is halted. In accordance with various embodiments, the system determines or confirms that the current has sufficiently dropped if the current falls below a current threshold, e.g., 4100 mA. As such, the system determines that the current condition has ceased and/or the tissue reached a vaporization or peak condition.

Figure 8:
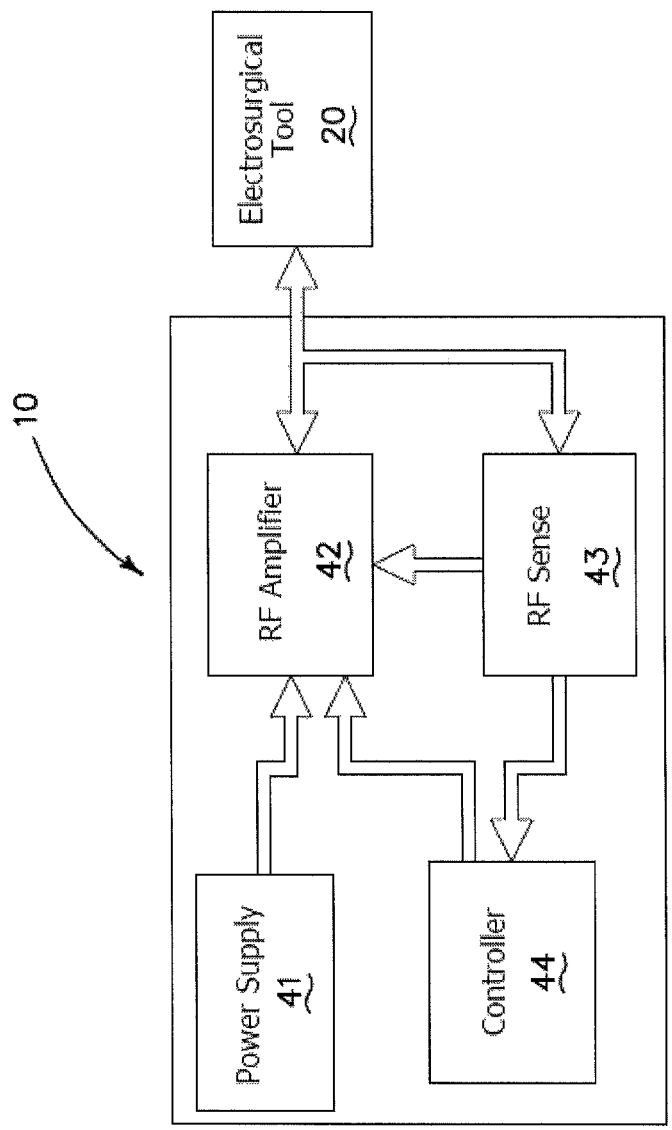
FIG. 8 is a schematic block diagram of portions of an electrosurgical system in accordance with various embodiments of the present invention.

Referring now to FIG. 8, in one embodiment, the electrosurgical generator 10 is connected to AC main input and a power supply 41 converts the AC voltage from the AC main input to DC voltages for powering various circuitry of the electrosurgical generator 10. The power supply also supplies DC voltage to an RF amplifier 42 that generates RF energy. In one embodiment, the RF amplifier 42 converts 100 VDC from the power supply to a sinusoidal waveform with a frequency of 350 kHz which is delivered through a connected electrosurgical instrument or tool 20. RF sense circuitry 43 measures/calculates voltage, current, power, and phase at the output of the electrosurgical generator 10 in which RF energy is supplied to the connected electrosurgical instrument or tool 20. The measured/calculated information is supplied to a controller 44.

In one embodiment, the RF sense 43 analyzes the measured AC voltage and current from the RF amplifier 42 and generates DC signals for control signals including voltage, current, power, and phase that are sent to the controller 44 for further processing. In one embodiment, RF sense 43 measures the output voltage and current and calculates the root means square (RMS) of the voltage and current, apparent power of the RF output energy, and the phase angle between the voltage and current of the RF energy being supplied through the connected electrosurgical instrument or tool 20. In particular, the voltage and current of the output RF energy are processed by analog circuitry of the RF sense to generate real and imaginary components of both voltage and current. These signals are processed by a field-programmable gate array (FPGA) to give different measurements relating to voltage and current, including the RMS measurements of the AC signals, phase shift between voltage and current, and power. Accordingly, in one embodiment, the output voltage and current are measured in analog, converted to digital, processed by an FPGA to calculate RMS voltage and current, apparent power and phase angle between voltage and current, and then are converted back to analog for the controller 44.

In one embodiment, controller 44 controls or signals the RF amplifier 42 to affect the output RF energy. For example, the controller 44 utilizes the information provided by the RF sense 43 to determine if RF energy should be outputted, adjusted or terminated. In one embodiment, the controller 44 determines if or when a predetermined current, power, and/or phase threshold has been reached or exceeded to determine when to terminate the output of RF energy. In various embodiments, the controller 44 performs a fusion or sealing process described in greater detail herein and in some embodiments the controller 44 receives the instructions, settings, or script data to perform the sealing process from data transmitted from the electrosurgical instrument or tool 20.

The RF Amplifier 42 generates high power RF energy to be passed through a connected electrosurgical instrument or tool 20. In one example, the electrosurgical instrument or tool 20 is used for fusing or sealing tissue. The RF Amplifier 42 in accordance with various embodiments is configured to convert a 100 VDC power source to a high power sinusoidal waveform with a frequency of 350 kHz. The converted power is then delivered to the connected electrosurgical instrument or tool 20. The RF Sense 43 interprets the measured AC voltage and current from the RF amplifier 42 and generates DC control signals, including voltage, current, power, and phase, that is interpreted by the controller 44.

The electrosurgical generator 10 (which includes the controller 44 and/or the RF sense 43) monitors and/or measures the RF energy being supplied to determine if it is as expected. In various embodiments, the system (e.g., the controller and/or RF sense), monitors the voltage and/or current of the RF energy to ensure the voltage and the current are above predefined threshold values. The system (e.g., the controller and/or RF sense), also monitors, measures, and/or calculates the phase and/or power of the supplied RF energy. The system (e.g., the controller and/or RF sense) ensures that the voltage, current, phase, and/or power of the supplied RF energy is within a predefined voltage, current, phase, and/or power window or range. In one embodiment, the voltage, current, phase, and/or power window are respectively delimited by a predefined maximum voltage, current, phase, and/or power and a predefined minimum voltage, current, phase, and/or power. If the voltage, current, phase, and/or power of the RF energy moves out of its respective window, an error is indicated. In one embodiment, the respective window slides or is adjusted by the system as RF energy is being supplied to seal the tissue between the jaws of the instrument. The adjustment of the respective window is to ensure that supplied RF energy is as expected. The system, in various embodiments, monitors the phase, and/or current or rate of phase, and/or current of the supplied RF energy to determine if the phase and/or current has reached or crossed a predefined phase and/or current threshold. If the phase and/or current crossing has occurred with respect to the predefined phase and/or current threshold, then the RF energy is supplied for a predefined time period before terminating.

In accordance with various embodiments, an operations engine of controller 44 enables the electrosurgical generator 10 to be configurable to accommodate different operational scenarios including but not limited to different and numerous electrosurgical instruments or tools, surgical procedures, and preferences. The operations engine receives and interprets data from an external source to specifically configure operation of the electrosurgical generator 10 based on the received data.

In accordance with various embodiments, the operations engine may receive configuration data from a database script file that is read from a memory device of the electrosurgical tool or instrument 20. The database script file defines the state logic used by the electrosurgical generator 10. Based on the state determined and measurements made by the electrosurgical generator 10, the database script file can define or set output levels as well as shutoff criteria for the electrosurgical generator 10. The database script file, in one embodiment, includes trigger events that include indications of a short condition, for example, when a measured phase is greater than 60 degrees, or an open condition, for example, when a measured current is less than 100 mA.

Figure 9:
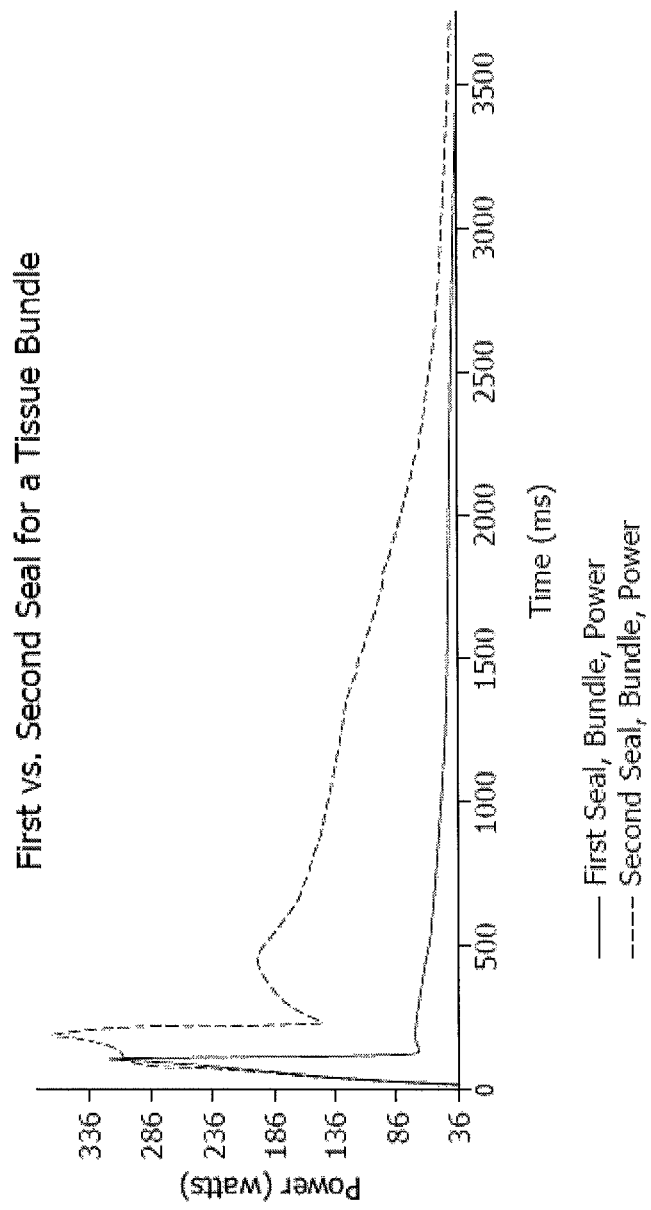
FIG. 9 is a graphical representation of samples of experimental data for a sealing process or aspects thereof with an electrosurgical system in accordance with various embodiments of the present invention.

In accordance with various embodiments, after the dynamic voltage ramp, tissue that draws a relatively low amount of current or power is small in volume or may be already highly desiccated as shown, for example, in FIG. 9.

The highly desiccated tissue can be commonly encountered in a double or repeated seal situation (e.g., when a surgeon activates the instrument to supply RF energy a second time after a first seal cycle or an already completed seal cycle without moving the instrument or positioning the instrument on different portions of the tissue or an entirely different tissue). Double or repeated seals results in an additional application of RF energy including heat and thereby increases potential eschar buildup, thermal spread, and/or adhesion. In various embodiments, the system reduces or prevents RF output with a high voltage when such repeated seals occur.

In accordance with various embodiments, the system identifies or determines a tissue's desiccation level in contact with the instrument. The system employs low levels of current or power, high levels of impedance, low phase angles, low energy delivery, and/or a lack of water vaporization (e.g., steam) during the seal cycle to identify a tissue's desiccation level. Once the desiccation level of the tissue has been identified, the RF output is reduced, such as providing RF energy for a limited time period or power level. In various embodiments, static thresholds can be used for any of these values to trigger conditions (e.g., 500 mA) and/or thresholds can be calculated during the seal cycle (e.g., 20% below a predicted maximum).

In various embodiments, the system uses one or more of these threshold values to distinguish already-sealed tissue and triggers early in the seal cycle. At the end of the seal cycle, first activations and subsequent activations can look very similar with the tissue being desiccated in both cases. However, at the beginning of the seal cycle, first activations will draw much more current or power since water is still present in the tissue (compared to subsequent seals which may not). In addition, as tissue seals, the current or power drawn can change substantially. An activation on an already-sealed tissue may have a much lower rate of change and as such, the system utilizes the derivative of measurement value of interest to be used to identify a meaningful change being made to the tissue.

In various embodiments, the system tracks phase of the RF output and in particular, at the beginning of a seal cycle, to identify repetitive seals and/or thin tissue. Double seals tend to have phase values of greater than 20 degrees. Once a repeated seal or piece of thin tissue is identified, an alternate RF path for that tissue can be applied.

In various embodiments, the system uses a cascade of phase values which adjusts the RF output depending on the magnitude of the initial phase. For example, if the phase is between 20 and 25 degrees, a modest reduction of RF energy is applied. However, if the phase is between 25 and 30 degrees, there is more certainty of the type of tissue in contact with the instrument, and thus RF energy being applied is reduced further or more aggressively. Continuing with this example, a phase angle over 30 degrees would provide the largest or most aggressive reduction in RF energy.

Once highly desiccated or thin tissue has been identified, any change in RF output that results in less heat being applied results in a better tissue sealing effects. Additional RF energy or no reduction in RF energy on this type of tissue can result in additional thermal spread, eschar, adhesion, and/or a longer procedure time without providing further benefits to hemostasis.

In accordance with various embodiments, the electrosurgical system comprising a double seal system that uses a threshold value to stop a voltage ramp, which results in in a lower hold voltage through the seal and/or uses a threshold value to terminate or halt the RF output and/or ending the seal cycle. In various embodiments, the double seal system also uses a threshold value to immediately leave a state, rather than reaching a timeout value and can result in a reduction in total seal time.

Figure 10:
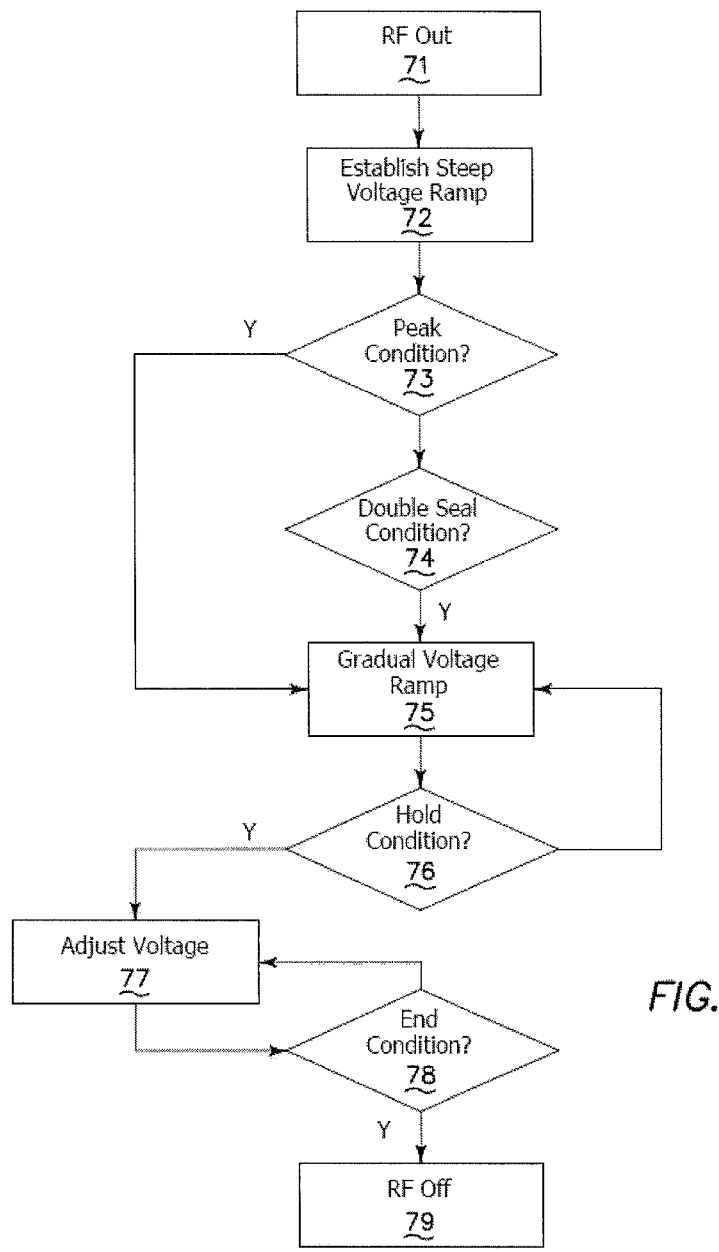
FIG. 10 is a flowchart illustrating operations of an electrosurgical system in accordance with various embodiments of the present invention.

Exemplary RF energy control process, script, or systems for the electrosurgical generator and associated electrosurgical tools for fusing or sealing tissue in accordance with various embodiments are shown in FIG. 10. In a first step 71, RF energy is supplied by the electrosurgical generator through the connected electrosurgical tool. The electrosurgical generator sets the voltage of the supplied RF energy in order to generate the RF energy having a steep ramp in step 72. In accordance with various embodiments, the RF energy that is provided or generated is a steep ramp with voltage increasing from a predefined initial value (e.g., 40V) to a maximum value (e.g., 60V) in a predefined time period (e.g., 75 ms) and/or with current increasing from a predefined initial value (e.g., 2500 mA) to a predefined maximum value (e.g., 5000 mA) in the same predefined time period (e.g., 75 ms). The electrosurgical generator or system determines or identifies an RF output peak condition in step 73 while continuing to supply RF energy in the ramping fashion performed in step 72.

In various embodiments, the system monitors or measures the current and/or power of the RF output in order to determine if the current and/or power is decreasing or has reached a predefined threshold. This is performed in order to further determine if a peak condition has been reached. If a peak condition is not identified or reached, the system determines if a double seal condition is present in step 74. In various embodiments, the system monitors or measures the current of the RF output and determines if the current is decreasing or has reached a predefined current threshold to determine if a double seal condition is present or identified. If the peak condition and/or a double or repeated seal is identified, the system alters or adjust to reduce the voltage of the RF output in step 75. In various embodiments, the system causes the RF energy to ramp gradually (in step 75), increasing from a predefined initial value (e.g., 35V) to a maximum value (e.g., 45V) over a predefined time period (e.g., 500 ms).

The electrosurgical generator or system monitors, determines, or identifies a hold condition in step 76 while continuing to supply RF energy in the ramping fashion as described in step 75 (above). The electrosurgical generator or system, in various embodiments, measures, calculates, and/or monitors at least the phase, voltage, current, power, and/or change/rate thereof of the supplied RF energy. If the condition (e.g., a phase and current condition) is reached or equals, exceeds or falls below a predetermined threshold or value in step 76, the RF output is adjusted in step 77. In various embodiments, the electrosurgical generator causes the voltage of the supplied RF output to be held constant and/or the ramp terminated. In various embodiments, if a phase condition or threshold is reached or falls below a predetermined phase threshold value and a current condition or value is reached or falls below a predetermined current threshold value, the electrosurgical generator adjusts the voltage of the supplied RF energy to be constant. If the phase and current condition or threshold is not reached or crossed, the electrosurgical generator waits a predefined time period while continuing to supply RF energy in the ramping fashion (via step 75) and monitoring for the hold condition (via step 76). With constant voltage (via step 77), the electrosurgical generator monitors, identifies, or determines an end condition (via step 78) while continuing to supply and/or adjust the RF energy being supplied (in step 77). If the end condition is determined or identified, the process is characterized as being done. Termination procedures are initiated and/or RF energy supplied by the generator is stopped (in step 79). If the power condition or threshold representing the end condition is reached or equals, exceeds or falls below a predetermined threshold or value, the process is characterized as being done. Termination procedures can then be initiated and/or RF energy supplied by the generator can be stopped. If the end condition or threshold is not reached or crossed, the electrosurgical generator continues to supply RF energy, while monitoring for the power condition.

In various embodiments, prior to the start of the process, impedance is measured to determine a short condition or open condition through a low voltage measurement signal delivered to a connected electrosurgical tool. In one embodiment, passive impedance is measured to determine if the tissue grasped is within the operating range of the electrosurgical tool (e.g., 2-200Ω). If the initial impedance check is passed, the RF energy is supplied to the electrosurgical tool, after which impedance/resistance is not measured again or ignored.

In various embodiments, the maximum current or power value is static or predetermined, stored in memory, or is provided or set through external inputs. In accordance with various embodiments, the maximum current or power value is determined by the system through the application of the RF energy and monitoring the current and/or power of the supplied RF energy to determine a current or power peak. In various embodiments, the maximum current or power value represents a vaporization point for the tissue in contact with the electrosurgical instrument. In various embodiments, the generator provides a high voltage steep ramp to bring the tissue to a water vaporization point quickly.

In accordance with various embodiments, a maximum phase value is determined by the system through the application of the RF energy and monitoring the phase to determine a phase peak representing an RF output peak condition. In various embodiments, a thermocouple or similar temperature sensor or detection system is provided with the instrument, such as a thermocouple embedded on the surface of a jaw, to monitor tissue temperature and potentially identify a rapid rise of temperature occurring until water vaporization begins, at which point a state change would stop the rise in temperature due to additional heat creating steam and thus an RF output peak condition can be identified. In accordance with various embodiments, a minimum impedance is determined by the system through the application of the RF energy and monitoring the tissue impedance to determine an impedance floor representing an RF output peak floor. As such, the process or system is somewhat inverted with a minimum value or window being determined rather than a maximum.

In various embodiments, the electrosurgical generator provides a high voltage ramp or pulse to bring the tissue to a RF output peak point or condition quickly. In various embodiments, the RF output peak condition represents or corresponds to a water vaporization point or condition, e.g., when the fluid in the tissue begins to change state and vaporize. This can be observed when steam starts being generated from the tissue being sealed. This point or condition, in various embodiments, is defined or identified when the power or current output of the RF energy being applied or supplied is at its greatest or reaches its peak. If the vaporization or peak point is not reached during the pulse (e.g., under-pulsing), then the subsequent drop in voltage and gradual ramp-up is delayed in this seal cycle. Tissue that is under-pulsed starts its effective seal cycle or removal of water much later than anticipated, resulting in less total water being removed in the same time period.

In accordance with various embodiments, the electrosurgical generator is configured to provide additional regulation of various parameters or functions related to the output of the RF energy, voltage, current, power, and/or phase and the operations engine is configured to utilize the various parameters or functions to adjust the output of the RF energy. In one exemplary embodiment, the control circuitry provides additional regulation controls for direct regulation of phase in which voltage, current, and/or power output would be adjusted to satisfy specified phase regulation set points provided by the operations engine.

In accordance with various embodiments, the generator utilizes the monitored, measured and/or calculated values of voltage, power, current, and/or phase (e.g., control indicators) to recognize and act/perform operation conditions. In various embodiments, additional measurements or calculations based on the measured values related to RF output regulation circuitry are provided by the script or operations engine to recognize and act upon additional or different events related to or trigger by the additional measurements or calculations relative to other measurements or thresholds. The additional measurements in one embodiment include error signals in combination with a pulse width modulation (PWM) duty cycle used to regulate the output of voltage, current and/or power or other similar regulation parameters. Different or additional events or indicators that could be identified and triggered in various embodiments could be transitions from one regulation control to another regulation control (e.g., current regulation to power regulation). In various embodiments, subsequent impedance or temperature checks or measurements may not be performed as such checks or measurements may be imprecise and/or impractical.

In various embodiments, the generator utilizes many states, control points, or checks to identify a phase, current, or power value and respectively for a positive or negative trend. An error is signaled if the electrosurgical generator does not identify an expected trend. The multistate checks increase or enhance the electrosurgical generator resolution in identifying an expected RF output trend over different types of tissue.

In various embodiments, the electrosurgical generator also monitors the phase or current and/or rate of phase or current to determine if the connected electrosurgical tool has experienced an electrical open condition or short condition. In one example, the electrosurgical generator identifies an electrical short condition of the connected electrosurgical instrument by monitoring the phase of the applied or supplied RF energy. If the monitored phase is greater than a predefined maximum phase value, an electrical short condition is identified. Similarly, in one example, the electrosurgical generator identifies an electrical open condition of the connected electrosurgical instrument by monitoring the current of the applied or supplied RF energy. If the monitored current is less than a predefined minimum current, an electrical open condition is identified. In either or both cases, the electrosurgical generator upon discovery of the open condition and/or short condition indicates an error and the RF energy being supplied is halted.

In various embodiments, the predefined process as described throughout the application is loaded into a memory module embedded into a connector removably connected to a plug and/or cable connection to an electrosurgical instrument. In various embodiments, the device script or process is programmed onto an adapter PCBA (Printed Circuit Board Assembly) contained within the device connector or hardwired into circuitry within the device connector or controller during manufacture/assembly. The script source file is written in a custom text-based language and is then compiled by a script compiler into a script database file that is only readable by the generator. The script file contains parameters specifically chosen to configure the generator to output a specific voltage (e.g., 100v (RMS)), current (e.g., 5000 mA (RMS)), and power level (e.g., 300VA). In various embodiments, a device key programmer device reads and then programs the script database file into the memory of the adapter PCBA.

Turning now to some of the operational aspects of the electrosurgical tool or instrument described herein in accordance with various embodiments, once a vessel or tissue bundle has been identified for fusing, the first jaw 31 and the second jaw 33 are placed around the tissue. The movable handle 23 is squeezed and thereby pivots the first jaw 31 and the second jaw 33 together to effectively grasp the tissue. The actuator 24 has a first or initial position in which the jaws 22 are in an open position with the movable handle 23 positioned away or spaced from the stationary housing 28.

The depression of the activation button 29 by the surgeon causes the application of the radio frequency energy to the tissue between the jaws 22. Once the tissue has been fused, the actuator 24 can be reopened by the movable handle 23 being released and moved away from stationary housing 28. To cut tissue between the jaws 22, the user can actuate the blade trigger 25. When the blade trigger is moved proximally, a cutting blade moves distally to divide the tissue between the jaws 22. When the surgeon releases the blade trigger 25, the blade spring resets the cutting blade to its original position. In accordance with various embodiments, the actuator 24 has a cut position in which the jaws 22 are in a closed position, the movable handle 23 is closed and latched and the blade trigger 25 has been depressed advancing the cutting blade to its distal most position.

In various embodiments, an intermediate or unlatched position is provided in which the jaws 22 are in a closed or proximate position but the movable handle 23 is unlatched. As such, if the movable handle 23 is released, the movable handle 23 will return to its original or initial position. In one embodiment, the blade trigger 25 may not be activated to cut tissue between the jaws 22 but the activation button or switch 29 may be activated to fuse tissue between the jaws 22. In various embodiments, a latched position is provided in which the jaws 22 are in a closed or proximate position and the movable handle 23 is latched. As such, if the movable handle 23 is released, the movable handle 23 will not return to its original or initial position. In one embodiment, the activation button or switch 29 may be activated to fuse tissue between the closed jaws 22 and/or the blade trigger 25 may be activated to cut tissue between the jaws 22.

As described, in accordance with various embodiments, the electrosurgical instrument has a first (open) state in which the jaws 22 are spaced from each other and thus the movable handle 23 is also spaced from the stationary housing 28. The electrosurgical instrument is thus positioned to grasp tissue between the jaws 22. In the second (intermediate) state of the instrument, the jaws 22 are proximate to each other to grasp tissue between the jaws 22 and likewise the movable handle 23 and the stationary housing 28 are proximate to each other. The surgeon can revert back from the second state to the first state by opening the jaws 22 and thus positioning the jaws 22 again to grasp the tissue or other tissue. In the third (closed) state of the electrosurgical instrument, the movable handle 23 is moved further closer to the stationary housing 28. In some embodiments, the movable handle 23 may latch to the stationary housing 28. Movement to the third state, tissue grasped between the jaws 22 can be cut through the activation of the blade trigger 25. Movement to the third state, in which the movable handle 23 is latched to the stationary housing 28, reduces the potential situations whereby the tissue is unintentionally released. Also, inadvertent cutting of tissue or cutting of tissue along the wrong tissue lines can be better avoided. Additionally, the third (closed) state allows the application of constant and continuous predefined compression or range of compression on the tissue between the jaws 22 before, during, and after the activation of the RF energy, thereby enhancing the sealing or fusion of the tissue between the jaws 22. In accordance with various embodiments, application of the RF energy can occur once the mobile handle 23 and jaws 22 are in at least the second state and once the activation button 29 is activated by the surgeon. In some embodiments, the application of the RF energy can occur when the mobile handle 23 and jaws 22 are in the third state and once the activation button 29 is activated by the surgeon.

It is noted that in various embodiments to avoid false readings, the electrosurgical generator does not measure resistance or impedance of the tissue during the supply of the RF energy to the tissue. In accordance with various embodiments, an electrosurgical system is provided that decreases thermal spread and provides efficient power delivery for sealing vessels or tissue in contact with a bipolar electrosurgical instrument through the controlled and efficient supply of RF energy.

As described throughout the application, the electrosurgical generator supplies RF energy to a connected electrosurgical instrument. The electrosurgical generator ensures that the supplied RF energy does not exceed specified parameters and detects faults or error conditions. In various embodiments, an electrosurgical instrument provides the commands or logic used to appropriately apply RF energy for a surgical procedure. An electrosurgical instrument for example includes memory having commands and parameters that dictate the operation of the instrument in conjunction with the electrosurgical generator. For example, the electrosurgical generator can supply the RF energy but the connected electrosurgical instrument decides how much or how long the RF energy is applied. The electrosurgical generator, however, does not allow the supply of RF energy to exceed a set threshold even if directed to by the connected electrosurgical instrument thereby providing a check or assurance against a faulty instrument command.

As described generally above and described in further detail below, various electrosurgical instruments, tools, or devices can be used in the electrosurgical systems described herein. For example, electrosurgical graspers, scissors, tweezers, probes, needles, and other instruments incorporating one, some, or all of the aspects discussed herein can provide various advantages in an electrosurgical system. Various electrosurgical instruments and generator embodiments and combinations thereof are discussed throughout the application. It is contemplated that one, some, or all of the features discussed generally throughout the application can be included in any of the embodiments of the instruments, generators and combinations thereof discussed herein. For example, it can be desirable that each of the instruments described include a memory for interaction with the generator as previously described and vice versa. However, in other embodiments, the instruments and/or generators described can be configured to interact with a standard bipolar radio frequency power source without interaction of an instrument memory. Further, although various embodiments may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components. Likewise, such software components may be interchanged with hardware components or a combination thereof and vice versa.

Further examples of the electrosurgical unit, instruments and connections there between and operations and/or functionalities thereof are described in U.S. patent application Ser. No. 12/416,668, filed Apr. 1, 2009, entitled "Electrosurgical System"; Ser. No. 12/416,751, filed Apr. 1, 2009, entitled "Electrosurgical System"; Ser. No. 12/416,695, filed Apr. 1, 2009, entitled "Electrosurgical System"; Ser. No. 12/416,765, filed Apr. 1, 2009, entitled "Electrosurgical System"; Ser. No. 12/416,128, filed Mar. 31, 2009, entitled "Electrosurgical System"; and Ser. No. 14/848,116, filed Sep. 8, 2015, entitled "Electrosurgical System"; the entire disclosures of which are hereby incorporated by reference as if set in full herein. Certain aspects of these electrosurgical generators, tools and systems are discussed herein, and additional details and examples with respect to various embodiments are described in US Provisional Application Nos. 61/994,215, filed May 16, 2014, entitled "Electrosurgical Fusion Device"; 61/944,185, filed May 16, 2014, "Electrosurgical Generator with Synchronous Detector"; 61/994,415, filed May 16, 2014, "Electrosurgical System"; and 61/944,192, filed May 16, 2014, entitled "Electrosurgical Generator", the entire disclosures of which are hereby incorporated by reference as if set in full herein.

The above description is provided to enable any person skilled in the art to make and use the surgical devices and perform the methods described herein and sets forth the best modes contemplated by the inventors of carrying out their inventions. Various modifications, however, will remain apparent to those skilled in the art. It is contemplated that these modifications are within the scope of the present disclosure. Additionally, different embodiments or aspects of such embodiments may be shown in various figures and described throughout the specification. However, it should be noted that although shown or described separately each embodiment and aspects thereof may be combined with one or more of the other embodiments and aspects thereof unless expressly stated otherwise. It is merely for easing readability of the specification that each combination is not expressly set forth. Also, embodiments of the present invention should be considered in all respects as illustrative and not restrictive.

The invention claimed is:

1. An electrosurgical generator for fusing or sealing tissue comprising:
    a controller configured to:
        instruct an RF amplifier to apply a first pre-determined amount of RF energy to an area of tissue,
        determine a desiccation level of the area of tissue affected by the applying of the first pre-determined amount of RF energy,
        instruct the RF amplifier to reduce the first pre-determined amount of RF energy being applied to the area of tissue to a second amount of RF energy based on the determined desiccation level,
        instruct the RF amplifier to increase an amount of RF energy being applied to the area of tissue from the second amount to a third amount, wherein a rate of ramping the increasing amount of RF energy being applied and the third amount of RF energy to be applied to the area of tissue are based on the determined desiccation level, and wherein the third amount is between the first amount of RF energy and the second amount of RF energy,
        instruct the RF amplifier to maintain the third amount of RF energy being applied to the area of tissue, and
        instruct the RF amplifier to terminate the application of the RF energy to the area of the tissue after a first pre-determined period of time has elapsed; and
    an RF amplifier configured to generate a corresponding amount of RF energy that is passed to an electrosurgical instrument connected to the electrosurgical generator, wherein the corresponding amount of RF energy generated is based on the instructions provided by the controller.

2. The electrosurgical generator of claim 1, wherein the electrosurgical instrument includes memory configured to store a script, wherein the script is downloaded from the memory of the electrosurgical instrument to the controller, and wherein the script includes instructions that configure the electrosurgical generator to generate pre-defined amounts of RF energy for the electrosurgical instrument.

3. The electrosurgical generator of claim 2, wherein the first, second, and third amount of RF energy generated by the RF amplifier is also based on associated surgical procedures being performed.

4. The electrosurgical generator of claim 2, wherein the first, second, and third amount of RF energy generated by the RF amplifier is also based on received user preferences, and wherein the received user preferences are obtained via user inputs associated with the electrosurgical generator.

5. The electrosurgical generator of claim 1, further comprising a user interface configured to receive user input, wherein instructions are generated that instruct the electrosurgical generator to generate an amount of RF energy based on the user input.

6. The electrosurgical generator of claim 1, wherein the first, second, and third amount of RF energy generated by the RF amplifier is also based on the type of electrosurgical instrument connected to the electrosurgical generator.

7. The generator of claim 1, wherein the first pre-determined amount of RF energy applied to the area of tissue by the RF amplifier has lower levels of current or power.

8. The generator of claim 1, wherein the first pre-determined amount of RF energy applied to the area of tissue by the RF amplifier has high levels of impedance.

9. The generator of claim 1, wherein the first pre-determined amount of RF energy applied to the area of tissue by the RF amplifier has low phase angles.

10. The generator of claim 1, wherein the first pre-determined amount of RF energy applied to the area of tissue by the RF amplifier has low energy delivery.

11. The generator of claim 1, wherein the determining of the desiccation level of the area of tissue by the controller includes identifying a current peak condition of the RF energy being applied to the area of tissue.

12. The generator of claim 11, wherein the determining of the desiccation level of the area of tissue by the controller further includes identifying that the current peak condition of the RF energy being applied to the area of tissue is less than a pre-defined threshold.

13. The generator of claim 12, wherein the pre-defined threshold corresponds to a double seal condition.

14. The generator of claim 12, wherein the identifying of the current peak condition includes:
establishing a break value that is based on a percentage of a maximum amount or window for voltage or current that can be applied to the area of tissue; and
detecting that a current voltage or current measurement is greater than the break value.

15. The generator of claim 14, wherein a difference between the first pre-determined amount of RF energy being applied to the area of tissue and the second amount of RF energy is based on the percentage used with establishing the break value.

16. The generator of claim 15, wherein an amount for higher percentages associated with establishing the break value is higher than a different amount that corresponds with lower percentages associated with establishing the break value.

17. The generator of claim 12, wherein the identifying of the current peak condition by the controller comprises:
monitoring a rate of change of the current and/or power of the RF energy being applied to the area of tissue; and
comparing the monitored rate of change with a pre-determined threshold that corresponds to an identification that the current peak condition is near or close to occurring.

18. The generator of claim 12, wherein the identifying of the current peak condition by the controller comprises:
regulating current associated with the RF energy being applied to the area of tissue;
detecting an increase in voltage greater than a pre-determined threshold voltage; and
associating a timing of the increase in voltage greater than the pre-determined threshold voltage with the current peak condition.

19. The generator of claim 1, wherein the determining of the desiccation level of the area of tissue by the controller includes identifying an amount of water vaporization during the seal cycle.

20. The generator of claim 19, wherein the amount of water vaporization is identified by the controller via an output of steam.

21. The generator of claim 1, wherein the second amount of RF energy that the controller instructs the RF amplifier to reduce from the first pre-determined amount of RF energy is based on a percentage associated with a predicted maximum amount of RF energy that can be applied to the area of tissue.

22. The generator of claim 1, wherein the second amount of RF energy that the controller instructs the RF amplifier to reduce from the first pre-determined amount of RF energy is a pre-set value.

23. The generator of claim 1, wherein the determining of the desiccation level by the controller includes identifying situations where the area of tissue has previously been fused or sealed.

24. The generator of claim 1, wherein the determining of the desiccation level by the controller includes identifying a thickness of the area of tissue.

25. The generator of claim 1, wherein the determining of the desiccation level by the controller includes identifying a volume of the area of tissue.

26. The generator of claim 1, wherein the first pre-determined amount of RF energy that the controller instructs the RF amplifier to apply to the area of tissue has a pre-determined slope voltage profile that corresponds to a pre-determined increase in voltage of the RF energy over a second pre-determined period of time.

27. The generator of claim 26, wherein the second pre-determined period of time is based on a surface area of the area of tissue.

28. The generator of claim 26, wherein the second pre-determined period of time includes a maximum time threshold that terminates the increase in voltage of the RF energy once the maximum time threshold is reached.

29. The generator of claim 1, wherein the first pre-determined period of time associated with maintaining the third amount of RF energy being applied to the area of tissue is based on characteristics of the area of tissue.

30. The generator of claim 29, wherein the characteristics of the area of tissue includes a thickness or a volume of the area of tissue.

31. The generator of claim 1, wherein the first pre-determined amount of RF energy being applied to the area of tissue as instructed by the controller to the RF amplifier is configured to heat the area of tissue to a pre-determined temperature of 100° C. to perform desiccation.

32. The generator of claim 1, wherein the third amount of RF energy applied to the area of tissue as instructed by the controller to the RF amplifier is configured to maintain a temperature of the area of tissue sufficient for continued desiccation.

33. The generator of claim 1, wherein the controller further instructing the RF amplifier to increase the amount of RF energy being applied to the area of tissue from the second amount to the third amount comprises:
monitoring a phase and current of the RF energy as the amount of voltage of the RF energy increases from the second amount;
detecting when the current falls and when the phase becomes capacitive; and
identifying the third amount based on when the detected current fall and capacitive phase occurs.

34. The generator of claim 1, wherein the controller is configured to identify the different desiccation levels for the area of tissue in order to identify associated different second and third amounts of RF energy being applied to the area of tissue and different rates of ramping the RF energy from the second and third amounts to desiccate the area of tissue.

* * * * *